(12) United States Patent
Pandit et al.

(10) Patent No.: US 8,926,886 B2
(45) Date of Patent: Jan. 6, 2015

(54) MULTICHANNEL COLLAGEN NERVE CONDUIT FOR NERVE REPAIR

(75) Inventors: Abhay Pandit, Galway (IE); Li Yao, Galway (IE); Anthony Windebank, Galway (IE)

(73) Assignee: National University of Ireland, Galway, Galway (IE)

( * ) Notice: Subject to any disclaimer, the term of this patent is extended or adjusted under 35 U.S.C. 154(b) by 124 days.

(21) Appl. No.: 13/087,017

(22) Filed: Apr. 14, 2011

(65) Prior Publication Data
US 2011/0276066 A1 Nov. 10, 2011

(30) Foreign Application Priority Data
Apr. 15, 2010 (EP) .................................... 10160062

(51) Int. Cl.
*B29C 67/24* (2006.01)
*A61L 27/24* (2006.01)
*A61L 27/54* (2006.01)

(52) U.S. Cl.
CPC .................. *A61L 27/24* (2013.01); *A61L 27/54* (2013.01); *A61L 2300/258* (2013.01); *A61L 2430/32* (2013.01)
USPC ........... 264/330; 264/241; 264/255; 264/260; 264/261; 264/262; 264/263; 264/271.1; 264/272.12; 264/272.13; 264/275; 264/277; 264/279; 264/279.1; 264/251; 264/628; 264/629; 264/630; 264/632

(58) Field of Classification Search
USPC ........... 264/330, 219–227; 514/17.2, 8.3, 8.4; 604/368; 606/229; 623/1.47, 917
See application file for complete search history.

(56) References Cited

U.S. PATENT DOCUMENTS

| | | | | |
|---|---|---|---|---|
| 4,280,954 A | * | 7/1981 | Yannas et al. | 530/356 |
| 5,026,381 A | * | 6/1991 | Li | 606/152 |
| 5,925,053 A | * | 7/1999 | Hadlock et al. | 606/152 |
| 2005/0020506 A1 | * | 1/2005 | Drapeau et al. | 514/21 |

OTHER PUBLICATIONS

Archibald et al., "A Collagen-Based Nerve Guide Conduit for Peripheral Nerve Repair: An Electrophysiological Study of Nerve Regeneration in Rodents and Nonhuman Primates", J. Comp. Neurology, 306:685-696 (1991).
Bellamkonda, "Peripheral nerve regeneration: An opinion on channels, scaffolds and anisotropy", Biomaterials, 27:3515-3518 (2006).
Ben-Silmane et al., "Characteristics of Polyester Arterial Grafts Coated with Albumin: The Role and Importance of the Cross-Linking Chemicals", Eur. Surg. Res., 20:18-28 (1988).
Bodine-Fowler et al., "Inaccurate projection of rat soleus motoneurons: A comparison of nerve repair techniques", Muscle & Nerve, 20:29-37 (1997).
Brushart et al., "Dispersion of Regenerating Axons Across Enclosed Neural Gaps", J. Hand Surgery, 20A(4):557-564 (1995).
Cavalcanti et al., "Low-intensity Treadmill Exercise-related Changes in Rat Stellate Ganglion Neurons", J. Neurosci. Res., 87:1334-1342 (2009).

(Continued)

*Primary Examiner* — Jeffrey Wollschlager
*Assistant Examiner* — Stella Yi
(74) *Attorney, Agent, or Firm* — Ascenda Law Group PC

(57) ABSTRACT

The present invention relates to the fabrication of multichannel nerve conduits for use in the repair of nerve injury. In particular, the invention relates to collagen multichannel nerve conduits which are suitable for use in repair of peripheral nerves.

23 Claims, 15 Drawing Sheets

(56) References Cited

OTHER PUBLICATIONS

Chau et al., "The cellular response to transglutaminase-cross-linked collagen", Biomaterials, 26:6518-6529 (2005).
Chen et al., "Transplantation of bone marrow stromal cells for peripheral nerve repair", Experimental Neurology, 204:443-453 (2007).
Chen et al., "An In Vivo Study of Tricalcium Phosphate and Glutaraldehyde Crosslinking Gelatin Conduits in Peripheral Nerve Repair", J. Biomed. Mater. Res. B: Appl. Biomater., 77B(1):89-97 (2006).
Chew et al., "Aligned Protein-Polymer Composite Fibers Enhance Nerve Regeneration: A Potential Tissue-Engineering Platform", Adv. Funct. Mater., 17(8):1288-1296 (2007).
Colin and Donoff, "Nerve Regeneration Through Collagen Tubes", J. Dent. Res., 63(7):987-993 (1984).
de Ruiter et al., "Two-dimensional digital video ankle motion analysis for assessment of function in the rat sciatic nerve model", J. Peripheral Nervous System, 12:216-222 (2007).
de Ruiter et al., "Methods for in vitro characterization of multichannel nerve tubes", J. Biomed. Mater. Res., 84A:643-651 (2008).
de Ruiter et al., "Accuracy of Motor Axon Regeneration across Autograft, Single-lumen, and Multichannel Poly(Lactic-co-glycolic Acid) Nerve Tubes", Neurosurgery, 63:144-155 (2008).
Duan and Sheardown, "Crosslinking of collagen with dendrimers", J. Biomed. Mater. Res., 75A: 510-518 (2005).
Dunn et al., "Collagen Implants in the Vitreous", Arch. Ophthal., 82:840-844 (1969).
English et al., "Treadmill Training Enhances Axon Regeneration in Injured Mouse Peripheral Nerves Without Increased Loss of Topographic Specificity", J. Comp. Neurology, 517:245-255 (2009).
Evans et al., "Bioactive poly(L-lactic acid) conduits seeded with Schwann cells for peripheral nerve regeneration", Biomaterials 23:841-848 (2002).
Evans et al., "Selective reinnervation: a comparison of recovery following microsuture and conduit nerve repair", Brain Research, 559:315-321 (1991).
Giannini and Dyck, "The Fate of Schwann Cell Basement Membranes in Permanently Transected Nerves", J. Neuropath. Exper Neurol., 49(6):550-563 (1990).
Iida et al., "Peripheral nerve ischemia: reperfusion injury and fiber regeneration", Experimental Neurology, 184:997-1002 (2003).
Jiang et al., "Maximum Number of Collaterals Developed by One Axon during Peripheral Nerve Regeneration and the Influence of That Number on Reinnervation Effects", Eur. Neurol., 58:12-20 (2007).
Jiao et al., "Chitosan/polyglycolic acid nerve grafts for axon regeneration from prolonged axotomized neurons to chronically denervated segments", Biomaterials, 30:5004-5018 (2009).
Kim et al., "The role of aligned polymer fiber-based constructs in the bridging of long peripheral nerve gaps", Biomaterials, 29:3117-3127 (2008).
Laquerriere et al., "Experimental evaluation of bilayered human collagen as a dural substitute", J. Neurosurg., 78:487-491 (1993).
Matsuda et al., "Bioadhesion of gelatin films crosslinked with glutaraldehyde", J. Biomed. Mater. Res, 45:20-27 (1999).
Matsumoto et al., "Peripheral nerve regeneration across an 80-mm gap bridged by a polyglycolic acid (PGA)-collagen tube filled with laminin-coated collagen fibers: a histological and electrophysiological evaluation of regenerated nerves", Brain Research, 868:315-328 (2000).

O'Callaghan et al., "Long-Term Treadmill Exposure Protects Against Age-Related Neurodegenerative Change in the Rat Hippocampus", Hippocampus, 19:1019-1029 (2009).
Özay et al., "Citicoline improves functional recovery, promotes nerve regeneration, and reduces postoperative scarring after peripheral nerve surgery in rats", Surgical Neurology 68:615-622 (2007).
Pieper et al., "Preparation of characterization of porous crosslinked collagenous matrices containing bioavailable chondroitin sulphate", Biomaterials 20:847-858 (1999).
Powell and Boyce, "EDC cross-linking improves skin substitute strength and stability", Biomaterials, 27:5821-5827 (2006).
Rodriguez et al., "Highly permeable polylactide-caprolacone nerve guides enhance peripheral nerve regeneration through long gaps", Biomaterials, 20:1489-1500 (1999).
Sakakima et al., "Different frequency treadmill running in immobilization-induced muscle atrophy and ankle joint contracture of rats", Scan. J. Med. Sci. Sports, 14:186-192 (2004).
Sabatier et al., "Treadmill training promotes axon regeneration in injured peripheral nerves", Experimental Neurology, 211:489-493 (2008).
Sorensen and Windebank, "Relative Importance of Basement Membrane and Soluble Growth Factors in Delayed and Immediate Regeneration of Rat Sciatic Nerve", J. Neuropath. Exper. Neurol., 52(3):216-222 (1993).
Freier et al., "Chitin-based tubes for tissue engineering in the nervous system", Biomaterials, 26:4624-4632 (2005).
Ta et al., "Neurotoxicity of oxaliplatin and cisplatin for dorsal root ganglion neurons correlates with platinum-DNA binding", NeuroToxicology, 27:992-1002 (2006).
Toba et al., "Evaluation of peripheral nerve regeneration across an 80-mm gap using a polyglycolic acid (PGA)-collagen nerve conduit filled with laminin-soaked collagen sponge in dogs", Int. J. Artif. Organs, 25(3):230-237 (2002).
van Wachem et al., "Biocompatibility and tissue regenerating capacity of crosslinked dermal sheep collagen", J. Biomed. Mater. Res., 28:353-363 (1994).
van Wachem et al., "Tissue regenerating capacity of carbodiimide-crosslinked dermal sheep collagen during repair of the abdominal wall", Int. J. Artif. Organs, 17(4):230-239 (1994).
Vleggeert-Lankamp et al., "Type grouping in skeletal muscles after experimental reinnervation: another explanation", Eur. J. Neurosci., 21:1249-1256 (2005).
Wang et al., "Dog sciatic nerve regeneration across a 30-mm defect bridged by a chitosan/PGA artificial nerve graft", Brain, 128:1897-1910 (2005).
Wang et al., "Enhanced nerve regeneration through a bilayered chitosan tube: The effect of introduction of glycine space in to the CYIGSR sequence", J. Biomed. Mater. Res., 85A:919-928 (2008).
Wissink et al., "Endothelial Cell Seeding on Crosslinked Collagen: Effects of Crosslinking on Endothelial Cell Proliferation and Functional Parameters", Thromb. Haemost., 84:325-331 (2000).
Yang et al., "Development and evaluation of silk fibroin-based nerve grafts used for peripheral nerve regeneration", Biomaterials, 28:5526-5535 (2007).
Yao et al., "Orienting Neurite Growth in Electrospun Fibrous Neural Conduits", J. Biomed. Mater. Res. Part B: Appl. Biomater., 90B:483-491 (2009).
Yao et al., "Effect of functionalized micropatterned PLGA on guided neurite growth", Acta Biomaterialia, 5:580-588 (2009).
Johnson and Soucacos, "Nerve repair: Experimental and clinical evaluation of biodegradable artificial nerve guides", Injury, Int. J. Care Injured, 39S:S30-S36 (2008).

\* cited by examiner

US 8,926,886 B2

MULTICHANNEL COLLAGEN NERVE CONDUIT FOR NERVE REPAIR

CROSS REFERENCE TO RELATED APPLICATION

This application claims priority to European Patent Application No. 10160062.5 filed on Apr. 15, 2010.

FIELD OF THE INVENTION

The present invention relates to the fabrication of multichannel nerve conduits for use in the repair of nerve injury. In particular, the invention relates to collagen multichannel nerve conduits which are suitable for use in repair of peripheral nerves.

BACKGROUND TO THE INVENTION

Peripheral nerve injuries can be caused by trauma and iatrogenic injury. Over 700,000 peripheral nerve injuries occur due to accidental trauma and during surgery in the US and Europe annually. In the majority of injuries the nerve ends cannot be opposed. There are currently two choices for repair in this situation. Though an autologous nerve graft is the gold standard of nerve graft repair, it has several disadvantages, including the need for an extra incision, loss of donor nerve function, mismatch in size between the donor nerve and the injured nerve, and a limited availability of donor nerve. The second promising alternative is to use a synthetic "nerve tube" as a conduit for regeneration. A variety of synthetic and natural biopolymers such as polyglycolic acid, polylactic acid, chitosan, alginate silk and their composites or derivatives, has shown varying levels of success and • aws [Jiao et al, 2009; Yang et al, 2007; Matsmoto et al, 2000; Evans et al, 2002; Toba et al, 2002; Thomas et al, 2005; Wang et al, 2005; Bellamkonda, 2006; Jiang et al, 2007].

The nerve tissue matrix is composed of basal lamina tubes around the axon-schwann cell unit and longitudinally oriented collagen fibrils. There is extensive and compelling evidence that the success of peripheral nerve regeneration depends on the extra-cellular matrix [Giannini et al, 1990; Sorenson et al, 1993]. Collagen, the main structural component of these structures, is an extracellular matrix (ECM) molecule which may have specific advantages over other synthetic and natural polymers since it possesses cell-adhesive and signalling domains that are critical for nerve regeneration. As collagen may present a highly relevant biological microenvironment for axonal growth, a range of collagen conduits have been developed for nerve regeneration studies [Archibald et al 1991; Collin et al, 1984; Laquerriere et al, 1993].

Previous nerve regeneration studies have been performed dominantly based on single channel conduits [Jiao et al, 2009; Yang et al, 2007; Matsmoto et al, 2000; Evans et al, 2002; Toba et al, 2002; Thomas et al, 2005; Wang et al, 2005; Bellamkonda et al, 2006; Jiang et al, 2007]. Fibrous structure and microgrooves have been investigated and introduced into the design of nerve conduits to improve axonal growth guidance [Chew et al, 2007; Yang et al, 2008; Kim et al, 2007; Yao et al, 2009 1, 2;]. However, regardless of surface microtopography, single-channel nerve tube repair may lead to inappropriate target reinnervation by the dispersion of regenerating axons across the graft. [Brushart et al, 1995; de Ruiter et al, 2008b]. Although a previous nerve repair study based on PLGA multichannel conduits indicated less axonal dispersion compared with single channel conduit, most PLGA conduits swelled and collapsed in the experimental time-frame (de Ruiter G et al, 2008b). Multichannel collagen conduits that resemble the structure of nerve multiple basal lamina tubes may limit the dispersion of regenerating axons and provide guidance for nerve growth. When fabricating the next generation of nerve conduits, several aspects need to be considered. These include the biocompatibility of the materials, and the customized mechanical and degradation properties. Single-channel collagen conduits that possess a mechanical strength and are easy to process have previously been used in nerve regeneration applications. Because the channels of multichannel collagen conduits are much smaller than single channel conduits, slight swelling and deformation may reduce channel cavities significantly and impede nerve growth. The fabrication of multichannel collagen conduits is challenging and needs to be well programmed and optimized.

A number of nerve conduits are FDA approved for relatively short nerve defects, such as Integra Neurosciences Type I collagen tube, NeuraGen™, Collagen Matrix Inc.'s neuroflex and Synovis Surgical Innovations Gem Neurptube™. These are single-channel tubes which are used only for small defects of several millimeters and do not address larger peripheral nerve injuries. In addition, axons regenerating across these single lumen tubes assume a dispersed direction, resulting in inappropriate target re-enervation and the co-contraction of opposing muscles or synkinesis. The advantage of multichannel nerve conduits is that the dispersion may be limited as they resemble the structure of nerve multiple basal lamina tubes.

The goal of this study was to develop a robust collagen-based nerve conduit with multiple dimensionally stable sub-millimeter diameter channels to facilitate nerve guidance and limit dispersion. Towards this goal, we developed an innovative multi-step (sequential) moulding technique to create 1-, 4-, and 7-channel conduits from a high concentration collagen solution. The conduits were crosslinked with (1-ethyl-3-(3-dimethylaminopropyl) carbodiimide (EDC) in N-hydroxysuccinimide (NHS)) to control the biodegradation rate and to limit swelling.

To examine biocompatibility of the crosslinked collagen, dorsal root ganglia were cultured on the substrates and axonal growth quantified. As mechanical robustness and elastic recoil of the conduits is essential for implantation and post-surgical success, the structural mechanical properties were characterized by tensile, compressive, and three-point bending tests. This combination of chemical, biological, and mechanical analyses is necessary to determine the optimal biomaterial design for implantation studies.

The conduits were implanted in a 1 cm defect of the rat sciatic nerve and nerve regeneration was evaluated using compound muscle action potential (CMAP) recordings, quantitative nerve morphometry and simultaneous retrograde axonal tracing studies.

OBJECT OF THE INVENTION

It is an object of the present invention to provide a nerve conduit suitable for the repair of peripheral nerves. Another object of the invention is to provide a biomaterial scaffold with favorable material and mechanical properties. A further object is to provide a multichannel collagen nerve conduit which has minimal swelling and deformation properties. A further object is to provide nerve conduits which can be adapted to incorporate therapeutic biomolecules. Still further objects are to provide conduits with low toxicity to surrounding tissue, and which will be biocompatible and biodegradable and which promote the growth of nerves in a regular and controlled manner. Another object is to provide a nerve conduit with a high mechanical strength.

SUMMARY OF THE INVENTION

According to the present invention there is provided a method of manufacturing a collagen multichannel nerve conduit comprising:—
(a) placing at least one elongate formers between two retainers of a multichannel nerve conduit mould such that the formers are held in a spaced-apart relationship to each other,
(b) pouring collagen solution over each former so that substantially all the former is coated,
(c) drying the collagen solution on the formers,
(d) repeating steps (a) to (c) with additional formers until as many formers have been used as the number of channels desired in the conduit,
(e) cross-linking the dried collagen on the formers, and
(f) washing the cross-linked collagen on the formers to remove residual cross-linking solution.

The invention also provides a method of manufacturing a collagen multichannel nerve conduit comprising:—
(a) placing at least one elongate former between the two end caps or retainers,
(b) pouring collagen solution over the former so that substantially all the former is coated,
(c) allowing the collagen solution on the former to dry,
(d) cross-linking the air dried collagen on the former,
(e) washing the cross-linked collagen on the former to remove the cross-linking agent.

One retainer is positioned at either end of the elongate former. The formers and the retainers thus act as a negative mould.

Further collagen solution may be poured around the dried collagen construct on the former and/or poured around the retainer.

The collagen concentration may be between 3 and 15 mg/ml, preferably 12 mg/ml. This high concentration collagen solution (12 mg/ml) can fabricate collagen conduit very efficiently.

The collagen may be air-dried.

The cross-linker may be selected from the group consisting of EDC, transglutaminase, glutaraldehyde, genepin, sulfonates including methyl sulfonate and trifluoromethyl sulfonate, malemide, polyethylene glycol dendrimeric systems such as 4S-StarPEG, dendritic polymers, hyper-branced dendritic polymers, formaldehyde, enzymatic cross-linker, glycation, glyceraldehydes, cyanamide, diimide, diisocyante, dimethyl adipimidate, carbodiimide and epoxy. The dried collagen may be cross-linked with a solution of 1-60 mM EDC and 1-30 mM NHS in 1-100 mM MES solution, preferably 30 mM EDC and 10 mM NHS in 50 mM MES solution.

Where EDC and NHS are used, the concentration used for cross-linking can affect the biocompatibility of the conduit. The DRG cell culture results showed that an EDC concentration ranging up to 60 mM does not significantly affect axonal growth. Additionally, the EDC/NHS concentration can affect the degradation rate of the conduit. The collagen conduit degradation properties can be adjusted by changing the EDC concentration in the range of up to 60 mM.

In an in vivo study, we used 30 mM EDC/10 mM NHS to crosslink the collagen conduit. At this cross-linking level, the conduit degradation rate is lowest with no significant negative effect on the conduit biocompatibility.

The washing step may be carried out with 0.1-0.2 M $NaH_2PO_4$ and distilled water. The conduits should be washed for at least 4 times for a total of 2 hours. After washing the collagen may be freeze dried on the former. The collagen nerve conduit may be removed from the former. The former may be a wire or spike, and may be metal or plastics. The former may be stainless steel or nitinol.

In the freeze-drying procedure, the wet samples (the collagen conduits fabricated on the formers) was frozen first in the chamber of a freeze-drying machine, then the air is evacuated from the chamber to remove the water. After the samples were freeze-dried, the formers are easily pulled out from the collagen conduits.

The nerve conduit may have a number of channels, such as 2-200 or more, preferably two or four or seven channels, but particularly preferred are four channels. Preferably, the channels are evenly sized and spaced apart. This is achieved by evenly spacing the formers and using formers of the same size. Four channel conduits provide good nerve regeneration results and also good results in limiting axonal dispersion. The fabrication of a 7-channel conduit is more complicated compared with 1-, 2-, and 4-channel conduits, but also gives reasonable results. The outer diameter of the nerve conduit can be up to 1 cm, with the inner diameter of channels ranging between 50 µm-4000 µm. For a 2 mm conduit, the inner diameter of channels may be 50-700 µm, preferably 530 µm.

Suitably the collagen is type I collagen such as bovine tendon collagen.

The method may further comprise tethering biomolecules to the collagen. The biomolecules may be selected from nucleic acids such as Plasmid DNA and siRNA, or peptides or laminin, and nerve growth factor (for example, NGF or NT3). The biomolecules such as peptides, growth factors or plasmid DNA can be loaded on the collagen conduits. In this approach, the molecules can physically diffuse and attach on the collagen conduits. In the in vivo condition, the growth factors or plasmid DNA can elute from the conduit and interact with tissue cells. Alternatively the chemical structure of collagen contains lots of carboxylic groups (—COOH) and amine groups (—$NH_2$) groups, which can covalently link to synthetic or natural polymers that can complex growth factors or plasmid DNA. Then growth factor or plasmid DNA could release in vivo with collagen degradation.

In another aspect the invention provides a crosslinked, multichannel collagen nerve conduit whenever produced by a method as described above.

DETAILED DESCRIPTION OF THE INVENTION

Materials and Methods
Fabrication of Multichannel Collagen Nerve Conduits

Figure 1:
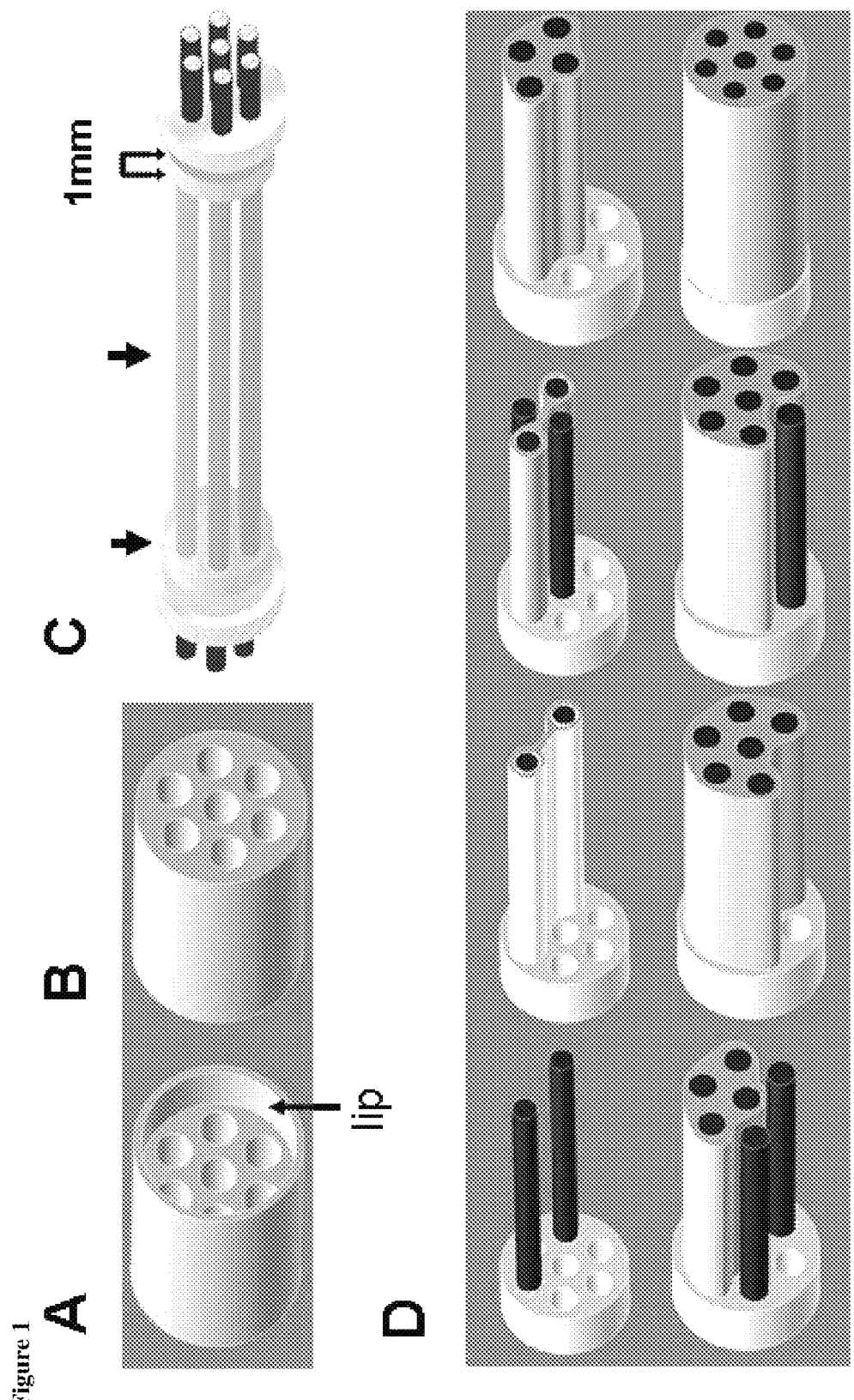
FIG. 1. Collagen conduits with (A) or without (B) the lip used for suturing during implantation. (C) Schematic of a 7-channel collagen conduit on the wire moulds with the end caps. The region of the collagen conduits and the moulds between the arrows are demonstrated at each fabrication stage in (D). (D) The step-by-step procedure of fabricating a 7-channel collagen conduit.

In this study, single- and multichannel conduits were designed with dimensions appropriate for a rat model of sciatic nerve repair. Cylindrical "negative" moulds were constructed with 4 or 7 wires spanning end caps or retainers to create channels for nerve guidance. Channel internal diameters (determined by the wire outer diameters) for 4- and 7-channel moulds were 530 µm and 410 µm, respectively. The distance between the two end caps of each mould was 1 cm. FIG. 1A shows a schematic of a 7-channel collagen conduit on a mould. For nerve repair, the conduits were fabricated with a 1 mm lip at each end (FIG. 1B) for insertion and suturing of the nerve stump. Conduits without lips were fabricated for in vitro characterization studies (FIG. 1C). The procedure for fabricating the 7-channel collagen conduit is shown schematically in FIG. 1D. Two stainless steel wires were inserted into channels in the two end caps and a 12 mg/ml collagen solution (derived from bovine Achilles tendon by pepsin and acid extraction) was allowed to self-assemble evenly on the wires and air-dried. An additional two wires were inserted into the two adjacent channels and collagen solution was allowed to self-assemble around the wires and air-dried. Two wires were inserted into the subsequent two channels of the two moulds and collagen solution was again placed around the wires and air-dried. Finally, one wire was inserted into the remaining channel of the two moulds and collagen solution was placed around the whole wire-dry-collagen construct. The collagen solution was allowed to self-assemble around the wire and air-dried (FIG. 1D). The 4-channel conduit was fabricated in an analogous manner with only 4 wires.

To fabricate a lip on the conduit for suturing, collagen solution was placed around the whole wire-dry collagen construct and also 1 mm of the retainers at each end (FIG. 1C). After removal of the wires and retainers, a lip is formed at each end of the conduit. The procedure for fabricating the 7-channel collagen conduit is shown schematically in FIG. 1D. Two stainless steel wires were inserted into channels in the two retainers or end caps and a 12 mg/ml collagen solution (derived from bovine Achilles tendon by pepsin and acid extraction) was allowed to self-assemble evenly on the wires and air-dried. An additional two wires were inserted into the two adjacent channels and collagen solution was allowed to self-assemble around the wires and air-dried. Two wires were inserted into the subsequent two channels of the two moulds and collagen solution was again placed around the wires and air-dried. Finally, one wire was inserted into the remaining channel of the two moulds and collagen solution was placed around the whole wire-dry-collagen construct. The collagen solution was allowed to self-assemble around the wire and air-dried (FIG. 1D).

To fabricate the 1-channel conduit, collagen solution was poured on a single stainless steel wire (diameter 1.5 mm) and air-dried. To enhance the mechanical strength of the conduit, the thickness of the wall of the conduit could be increased by placing more collagen around the whole wire-dry-collagen conduit and then air-dried.

The air-dried collagen conduit on the wires was then treated with a crosslinking solution of EDC (10, 30, or 60 mM) and NHS (1-30 mM) in MES solution (1-100 mM; pH 5.5) overnight. After washing with $NaH_2PO_4$ (0.1-0.2 M) and distilled water, the collagen was freeze-dried on the wires. Moulds and wires were removed from the collagen conduits after freeze-drying.

Collagen films were fabricated by spreading the collagen solution on a flat Teflon surface (weigh boat) and air-dried. The collagen films were then crosslinked with EDC and NHS as above. NeuraGen® collagen nerve conduits (NeuraGen®, Integra Life Sciences Corporation, USA), which have been used in clinical practice, served as control single-channel conduits.

Terminology

The non-crosslinked collagen film, 1-, 4- and 7-channel collagen conduits are named as CF, C1, C4 and C7 respectively. The collagen film, 1-, 4- and 7-channel collagen conduits that are crosslinked with 10 mM EDC/10 mM NHS, 30 mM EDC/10 mM NHS or 60 mM EDC/10 mM NHS are named as 10CF, 10C1, 10C4, 10C7, 30CF, 30C1, 30C4, 30C7, 60CF, 60C1, 60C4 and 60C7 respectively.

Collagenase Degradation

Figure 2:
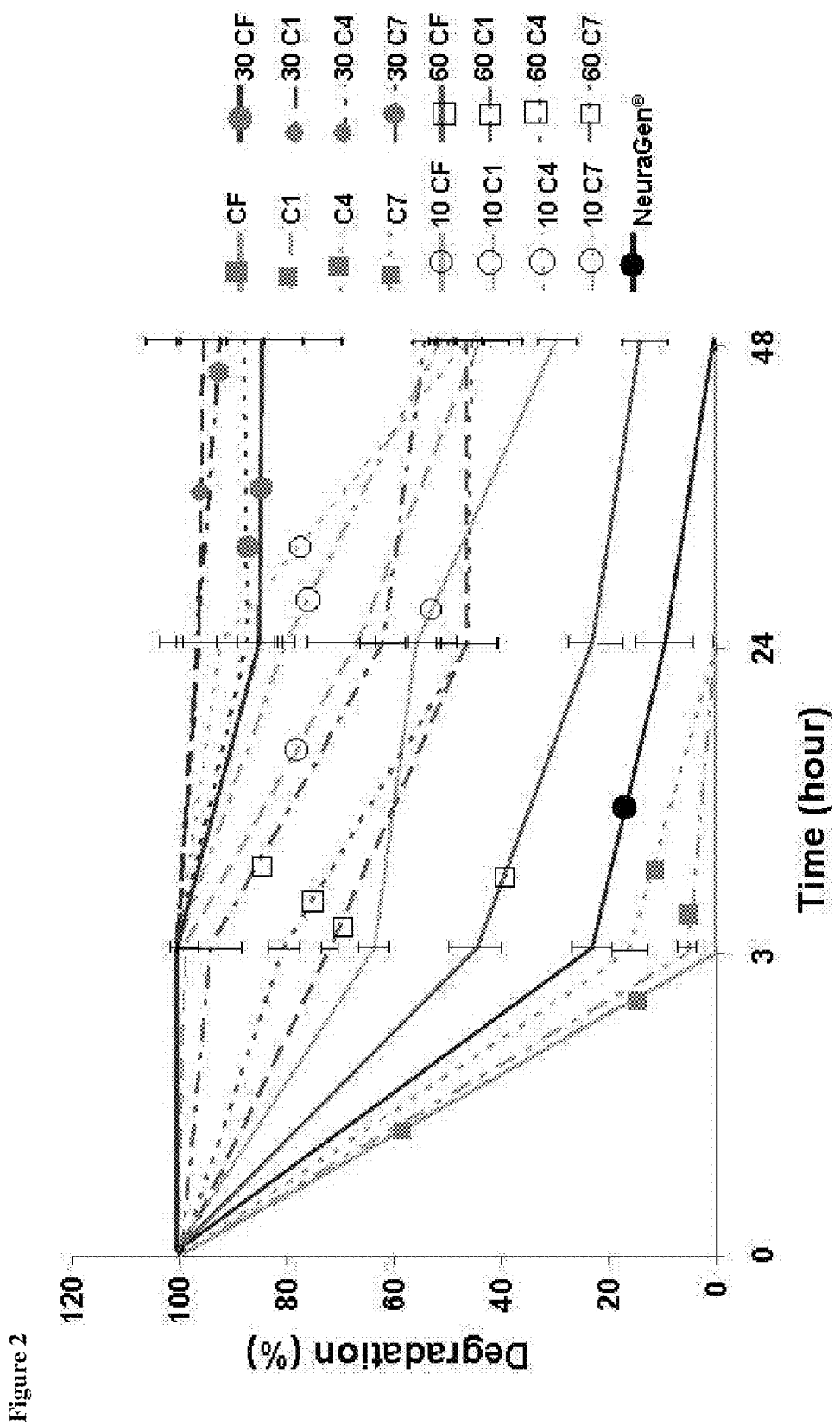
FIG. 2. Percentage degradation of collagen samples after 48 hours exposure to collagenase solution at 37° C. demonstrating high stability of 30 mM EDC crosslink.

The bacterial collagenase Type II enzyme derived from Clostridium histolyticum (Sigma:C6885, EC 3.4.24.3) was used to study the degradation profile of collagen conduits. The enzyme was dissolved in a 0.1 M Tris-HCl buffer (pH 7.4) solution containing 0.005 M $CaCl_2$ and 0.05 mg/ml $NaN_3A$ concentration of 5 U of collagenase per mg of collagen sample was used. After 3 hour, 24 hour and 48 hour incubation of the samples with enzyme solution, the samples were centrifugated at 4° C. and the remaining pellet was repeatedly washed with distilled water and then freeze-dried. The samples were then weighed. FIG. 2 illustrates the percentage degradation of the collagen and crosslinked collagen samples in the presence of collagenase enzyme as a function of time.

Free Amine Group Content

Collagen conduits and collagen film treated with different concentrations of EDC and NHS were cut into a weight of about 2 mg and placed into eppendorf tubes 200 µL of distilled water and 1 ml of ninhydrin solution was added to each tube. The tubes were incubated in the dark at 95-100° C. for 30 minutes. They were then allowed to cool to room temperature. 250 µL of each sample was added to 1 ml of 50% isopropanol solution. The solutions were then vortexed and assayed using the nanodrop at a wavelength of 570 nm. The ninhydrin solution was prepared by mixing one tube of 4% ninhydrin in 2-ethoxyethanol and another tube of 200 mM Citric acid (0.16 w/v % Tin II Chloride, pH 5.0). The contents of the two tubes were mixed thoroughly and immediately added to the samples.

Shrink Temperature

The shrink temperature of the collagen conduit and film samples was determined using differential scanning calorimetry (DSC). Calorimetric measurements were performed using a DSC-60 machine (Shimadzu Europe Ltd., Duisburg, Germany). Collagen conduit samples (6 mg) were immersed in PBS at 4° C. overnight. The wet samples were wiped with filter paper to remove excess water and hermetically sealed in aluminum pans. Heating was maintained at a rate of 5° C./min in the temperature range 25-95° C. with an empty aluminum pan as the reference probe. Shrink temperature (Ts) was determined as the onset value of the occurring endothermic peak. Three independent samples per matrix composition were measured.

Effect of EDC and NHS Crosslinking on Neurite Outgrowth from Dorsal Root Ganglia Procedures used in animal experiments were approved by the Institutional Animal Care and Use Committee and completed at the Mayo Clinic (Rochester, Minn., USA). Dorsal root ganglia (DRGs) from 14 day old rat embryos were isolated and cultured on CF, 10CF, 30CF, 60CF films. After 2 days of culture in MEM (minimum essential medium, GIBCO) supplemented with 10% calf serum, nerve growth factor (NGF, 8 ng/mL), glucose (0.6% w/v), and L-glutamine (1.4 mM; Sigma) at 37° C.), the DRGs were fixed with 4% paraphormaldehyde. The DRG cultures were then incubated with anti-tubulin III antibody (1:200, MsX Tubulin BetaIII Isoform, Milipore) overnight at 4° C. After washing, the cells were incubated with Cy3-cojugated goat anti-mouse IgG (1:200, Jackson ImmunoResearch) for 2 hours at room temperature. Images of DRGs were taken with a fluorescent microscope (Axiovert 200M; Carl Zeiss, Inc.).

Measurements of radial neurite outgrowth were performed using NIH Image J software. Neurite length was measured from the centre of the ganglion to the edge of the longest neuronal process as previously described [Ta, 2006]. Average neurite length (in mm) was calculated from the explants from three independent experiments.

Conduit Swelling

30C1, 30C4 and 30C7 conduits and Integra collagen conduit were placed in phosphate buffered solution (PBS, pH 7.4) at 37° C. The weight, length, width and channel area of the conduits were studied at time points of immediately before incubation and at day 1, day 7 and day 30 after incubation with PBS at 37° C. The length and width of conduits were measured with a digital caliper (Mitutoyo, Aurora, Ill., USA). The channel area was analyzed with an Image J software (National Institute of Mental Health, Bethesda, Md., USA). Images of collagen conduits at above time points were taken using a stereomicroscope (Nikon SMZ800, Nikon corporation, Japan) with a digital camera (Nikon digital sight DS-Fil camera, Nikon corporation, Japan).

Mechanical Characterisation Studies

Mechanical properties of multichannel collagen conduits were characterized by compressive, tensile, and 3-point bending tests. The compressive and tensile tests were performed on 30C1, 30C4, 30C7 collagen and commercial conduits using a uniaxial test machine (ELF 3200 Endura-Tec, Schaumburg, Ill.), and three-point bending tests were carried out using a dynamic mechanical analyzer (DMA 2980, TA Instruments, New Castle, Del.). The samples were incubated in PBS (37° C.) overnight before testing. All tests were performed immediately after the samples were taken out from the incubator.

The transverse compression test was performed on conduits with a length of 10 mm. The average diameters of 30C1, 30C4 30C7 and commercial conduits were 2.29±0.02 mm, 1.83±0.01 mm, 1.81±0.04 mm, 1.80±0.03 mm, respectively.

A displacement perpendicular to the longitudinal axis of conduit was applied at a crosshead speed of 6 mm/min to a final displacement of 1.2 mm (approximately 60% of the diameter of the conduits), and the force, F, and displacement, d, were recorded. The transverse compressive structural stiffness was calculated from the initial linear portion of the F-d curve using linear regression.

To carry out the tensile test, each collagen conduit was placed in the thumbscrew clamps. The distance between the clamps was set at 10 mm, and the conduits were stretched at a speed of 10 mm/min while recording force and displacement. The tensile structural stiffness was calculated from the initial linear portion of the F-d curve using linear regression and the strength was recorded as the highest force achieved during the test.

Figure 10:
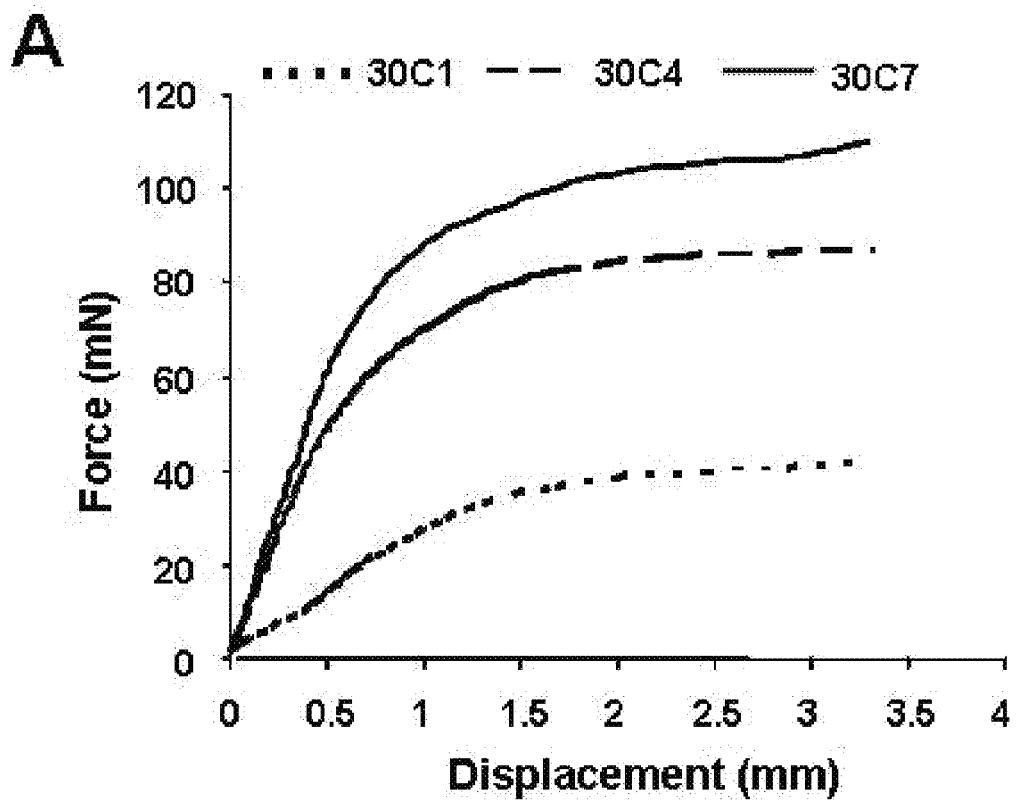
FIG. 10. Three-point bending test of collagen conduits. (A) Representative load-displacement curve of 3-point bending for each type of collagen conduit. (B) Bending stiffness of crosslinked collagen conduits. *, p<0.01.
Figure 10:
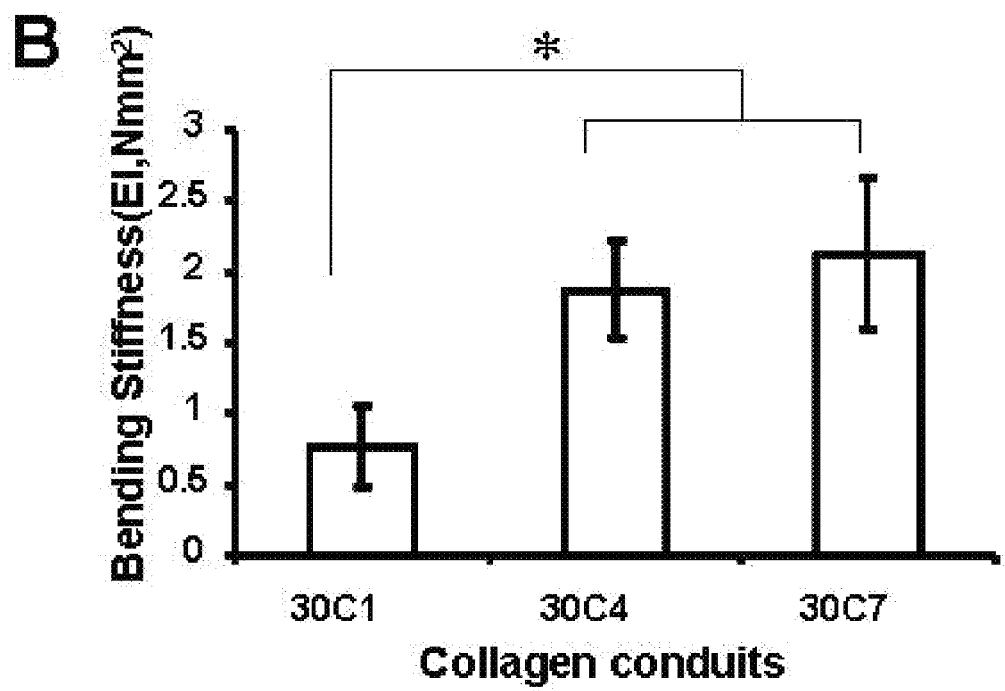

For the three-point bending tests, intact 15 mm conduits were placed into the holder at two points 1 cm apart (i.e., L=10 mm). At a third point midway between these, an increasing load was applied on the sample from above (FIG. 10A). The bending stiffness, EI, was calculated using the following formula:

$$EI=(F/d)(L^3/48)$$

where the best estimate of the slope (F/d) was determined by linear regression from the initial (linear) portion of the force-displacement curve.

Animals Procedures and Experimental Groups

In this study a total of 72 adult female Lewis rats, weighing between 190-220 gr, were used. In the first experimental group, for the study of nerve morphometry and CMAP recording, 48 rats were randomly assigned to 6 subgroups: autograft, 1-, 2-, 4- and 7-channel collagen conduits, and the commercial single channel collagen conduit (NeuraGen®, Integra Life Sciences Corporation, USA). In the second experimental group, for the study of simultaneous retrograde tracing, ankle motion analysis and CMAP recording, 24 rats were randomly assigned to four subgroups: autograft, 1-, 2- and 4-channel conduits. In this latter group, treadmill training (running speed 15 m/min, duration 10 minutes) was performed, one week post operation, and then four times per week for eight weeks in total to prevent formation of contractures.

Surgical Procedure

Rats were anesthetized using 80 mg/kg of ketamine and 5 mg/kg of xylazine, that was injected intraperitoneally. Dissection was performed with the aid of a Zeiss operating microscope (Carl Zeiss, Inc., Oberkochen, Germany). The left sciatic nerve was exposed and isolated at the midthigh level using a dorsal-lateral approach. A 5 mm segment of the sciatic nerve was resected before the bifurcation of the nerve into the tibial and peroneal nerve branches. The proximal and distal nerve ends were inserted 1 mm into the 12 mm long tubes with 10-0 monofilament nylon sutures (Ethilon; Ethicon, Inc., Piscataway, N.J.). The wound was subsequently closed in layers (Supplemental FIG. 1). The same procedure was performed for autologous nerve graft repair, except that a 1 cm segment of sciatic nerve was transected and microsurgically repaired with 10-0 monofilament nylon sutures.

Nerve Morphometry

After 16 weeks of implantation, in all animals of the first experimental group, the graft was re-exposed and fixed in situ with a Trump solution (4% formaldehyde and 1% glutaraldehyde in phosphate buffered solution) for 30 minutes The graft was resected and placed in the same fixative overnight. Specimens (2 mm) at the midpoint of the graft were collected and embedded in spur resin. Sections (1 µm) were cut with a glass knife on an ultramicrotome (Leica EMUC6 ultracut, Wetzlar, Germany). The sections of each specimen were stained with toluidine blue or 1% phenylenediamine for nerve morphometry. Nerve morphometry was performed on a image analysis system. Briefly, the inner and outer border of myelinated fibers was manually drawn for at least 500 myelinated fibers at 63× magnification in randomly selected areas in the slide to determine the number of myelinated fibers, the density of myelinated fibers, the mean diameter of myelinated fibers and the mean myelin thickness.

Compound Muscle Action Potential Recording

In all animals of both experimental groups, CMAPs were recorded before operation, 6, 8, 10, 12 and 16 weeks after nerve conduit implantation. Briefly, animals were first anesthetized with the procedure described above (surgical procedure), then CMAPs were recorded with an electromyography machine (Nicolet Viking IV; Viasys Healthcare, Inc., Conshohocken, Pa.) in the tibial and peroneal nerve-innervated foot muscles of the left limb. Needle recording electrodes were placed in the plantar or dorsal foot muscles referenced to needle electrodes placed distally in the foot digits. Needle-stimulating electrodes were placed directly posterior to the tibia with approximately 5 mm between the distal cathode and proximal anode. The stimulating electrodes were adjusted locally to produce the maximal CMAP amplitude. The stimulus was increased incrementally to produce a supramaximal response. CMAPs were recorded and analyzed for the amplitude of the action potential.

Simultaneous Retrograde Tracing

In the second experimental group, after sixteen weeks, all animals were anesthetized for simultaneous retrograde tracing The nerve graft and distal tibial and peroneal nerve branches were exposed. First the peroneal nerve was transected and the proximal end was placed in a cup with 5% diamidino yellow (DY) (EMS-Chemie, Mannedorf, Switzerland) solution for 20 minutes. After that, the nerve end was cleaned, then sutured into and covered by surrounding fat tissue to prevent tracer leakage and cross-contamination. Then the tibial nerve was transected and the proximal nerve end was placed in a cup with 5% fast blue (FB) (EMS-Chemie, Mannedorf, Switzerland) solution for 20 minutes. Again, the nerve end was cleaned and then sutured into and covered by surrounding fat tissue. Six days after tracer application, the animals were transcardially perfused with 4% paraphormaldehyde and 10% sucrose in phosphate buffered solution (PBS). Spinal cord segments L1 to L6 were removed and post-fixed overnight. Sagittal longitudinal 30 µm-thick sections were cut on a cryostat (LEICA Cryostat, CM3050S, Nussloch, Germany) at −20° C. Sections were immediately evaluated under a fluorescent microscope (Axioplan 2; Carl Zeiss, Inc.). Neuronal profiles with blue cytoplasm and a dark nucleus were counted as FB-labeled, profiles with a yellow nucleus and dark cytoplasm as DY-labeled, and profiles with a yellow nucleus and blue cytoplasm as FB-DY-double-labeled profiles. All profiles in all sections were counted.

Statistics

The data were expressed as means±SD and analyzed by using oneway ANOVA with a SPSS17.0 software package (SPSS Inc., Chicago, Ill., USA). P values less than 0.05 were considered statistically significant.

Results

Figure 3:
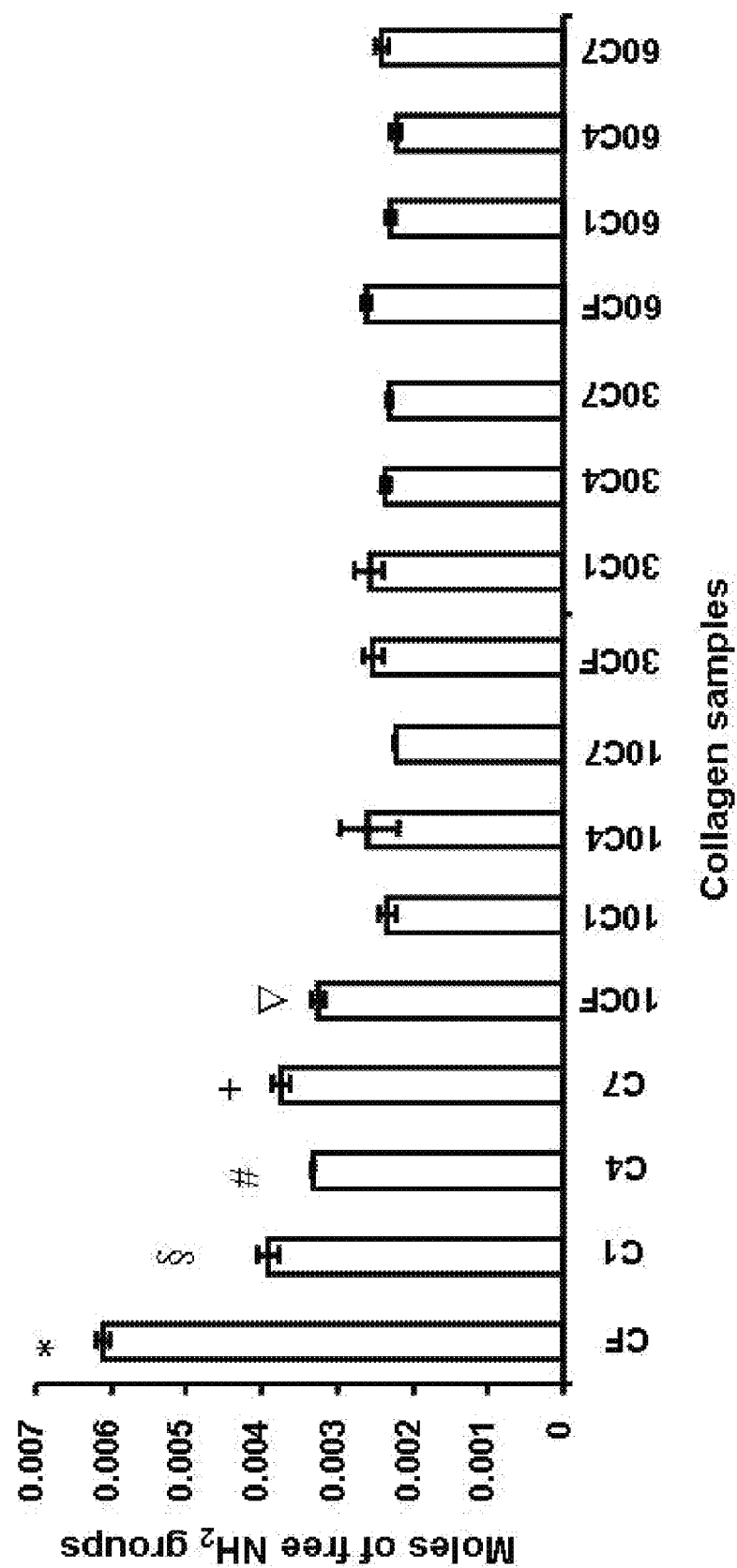
FIG. 3. Moles of free $NH_2$ groups from ninhydrin assay on collagen films and conduits. (*, $p<0.01$ vs all; §, $p<0.01$ vs all except C7; #, $p<0.01$ vs all except C7 and 10CF; +, $p<0.01$ vs all except C1 and C4; ∇, $p<0.05$ vs all except C4.)
Figure 4:
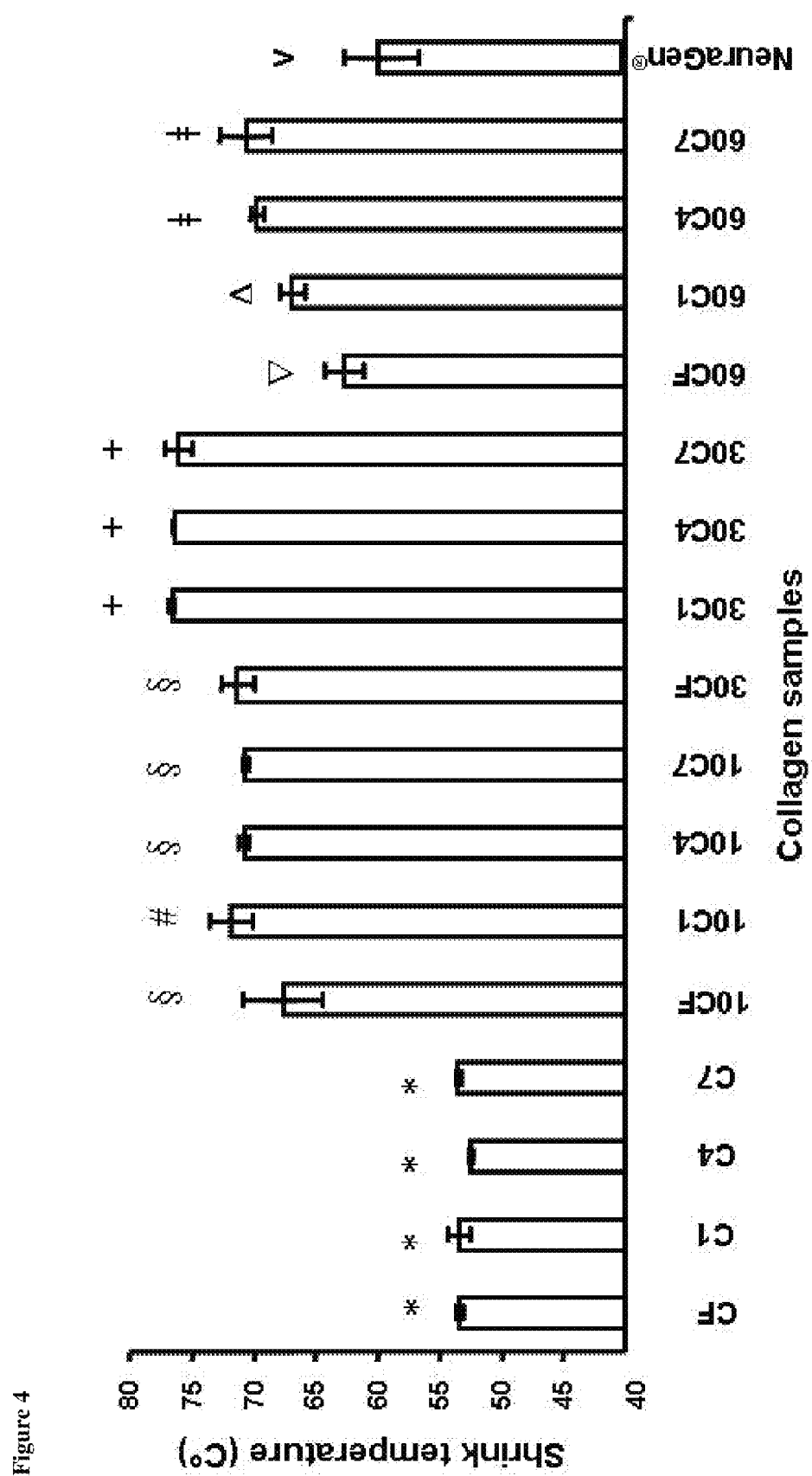
FIG. 4. Shrink (denaturation) temperatures for collagen films and collagen nerve conduits from DSC measurements demonstrating high stability of 30 mM EDC crosslinking (*, $p<0.05$ vs all; §, $p<0.05$ vs all except 60C1, 60C4 and 60C7; #, $p<0.05$ vs CF, C1, C4, C7, 30C1, 30C4, 30C7, 60CF, 60C1, NeuraGen®; +, $p<0.05$ vs all; ∇, $p<0.05$ vs all except 60C1; •, p<0.05 vs all except 10CF, 10C1, 10C4, 10C7, 60CF, 60C4, 60C7; •, p<0.01 vs CF, C1, C4, C7, 30C1, 30C4, 30C7, 60CF, NeuraGen®; v, p<0.01 vs all except 60CF)

Multichannel Collagen Conduits Crosslinked with 30 mM EDC and 10 mM NHS Showed Low Amine Content, High Thermal Stability and Maximal Collagenase Resistance The percentage weight of collagen samples remaining after collagenase degradation as a function of time is shown in FIG. 2. Crosslinking with EDC and NHS significantly reduced the collagenase degradation rate of collagen conduits. After 3 hours digestion, the weight of non-crosslinked collagen films, conduits and commercial conduit decreased significantly when compared with collagen conduit and films crosslinked with EDC/NHS (P<0.01). The degradation rate of 30C1, 30C4 and 30C7 conduits was significantly lower than that of all the other samples after 48 hours of digestion (P<0.01). The weight of all the crosslinked collagen conduits reduced at a lower rate at all the time points compared with that of the crosslinked collagen film and commercial collagen conduit (P<0.01). Crosslinking with EDC/NHS reduced the number of free amine groups from collagen conduits due to amide bonds formed between amine and carboxyl groups. The results of the quantitative assessment of amine content are shown in FIG. 3. The CF film showed significantly higher free amine groups (6.11±0.08 mmol) when compared with the EDC/NHS crosslinked collagen films and conduits and the non-crosslinked collagen conduits (P<0.01). The non-crosslinked collagen conduits and 10CF film showed significantly higher free amine groups than the 30CF, 60CF and all the crosslinked conduit (P<0.05). There was no statistical difference between the 10, 30 and 60 mM EDC-crosslinked conduits. The shrink temperatures of non-crosslinked collagen conduits and films were significantly lower than the crosslinked collagen conduits and films (P<0.01) and the commercial conduit (P<0.05) (FIG. 4). The shrink temperature of collagen conduits crosslinked with 30 mM EDC and 10 mM NHS were significantly higher than those of all the other samples (P<0.05). The commercial conduit and 60CF film showed significantly lower shrink temperatures than that of the other crosslinked collagen conduits and films (P<0.05).

Figure 5:
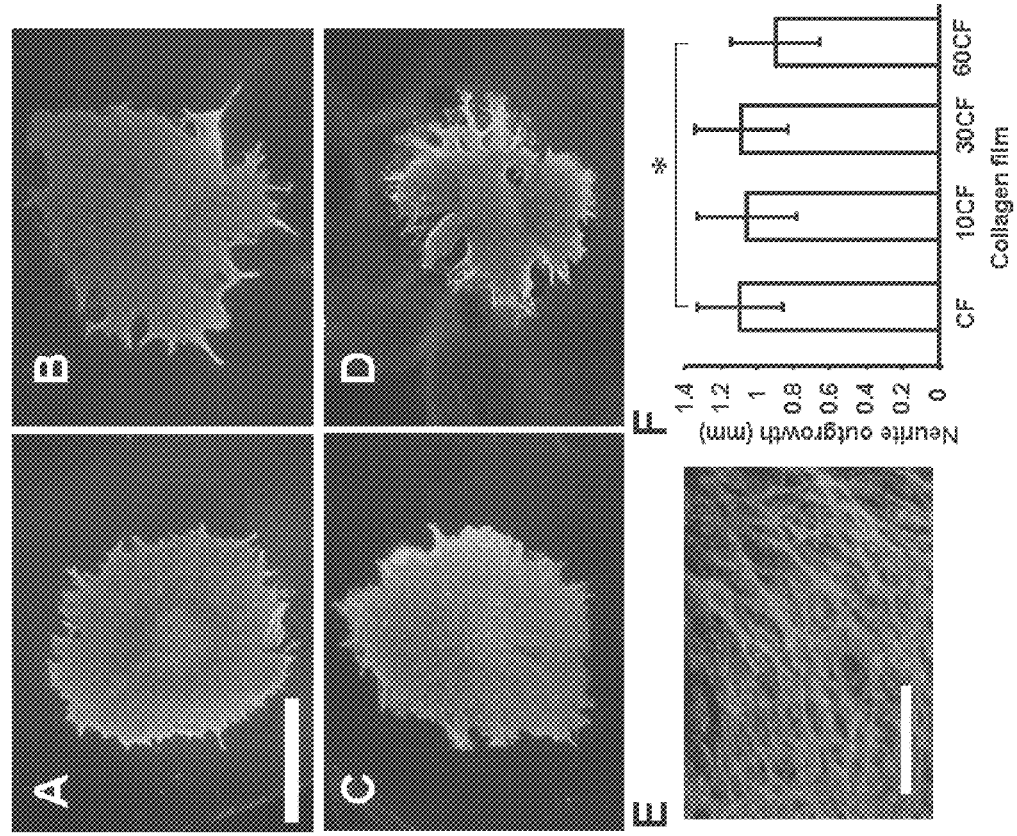
FIG. 5. Neurite outgrowth from dorsal root ganglia (DRGs) after two days of culture on EDC and NHS crosslinked collagen films. DRG image on non-crosslinked collagen film (A) and on 10CF (B), 30CF (C) and 60CF (D) films. Scale bar in (A), 1 mm (same scale for B, C and D). (E) Axonal growth from a DRG growing on 30CF film. Scale bar, 200 µm. (F) Analysis of neurite length from DRGs that were cultured on crosslinked collagen films. (*, p<0.05; n>20 per group).

Crosslinking With EDC Up to 30 mM Did Not Adversely Influence Axonal Outgrowth from DRG Explant Culture EDC/NHS crosslinked collagen films supported the outgrowth of DRG explants. The cell morphology in FIG. 5 demonstrates that DRGs grew on the crosslinked and non-crosslinked collagen films and extended neurites. The DRG explants showed similar neurite length when cultured on CF films, 10CF films and 30CF films, while on 60CF films the neurite length was shorter (FIG. 5A-E). The average neurite length for the DRGs growing on CF films (1.09±0.23 mm) was significantly higher than 60CF films (0.89±0.24 mm, P<0.05) but no other significant differences were found (FIG. 5F). Over 20 DRGs were used for the neurite length measurement in each group (N=26, 22, 23 and 30 for CF, 10CF, 30CF and 60CF, respectively).

Multichannel Collagen Conduits Maintained Channel Geometry in Swelling Studies

Figure 6:
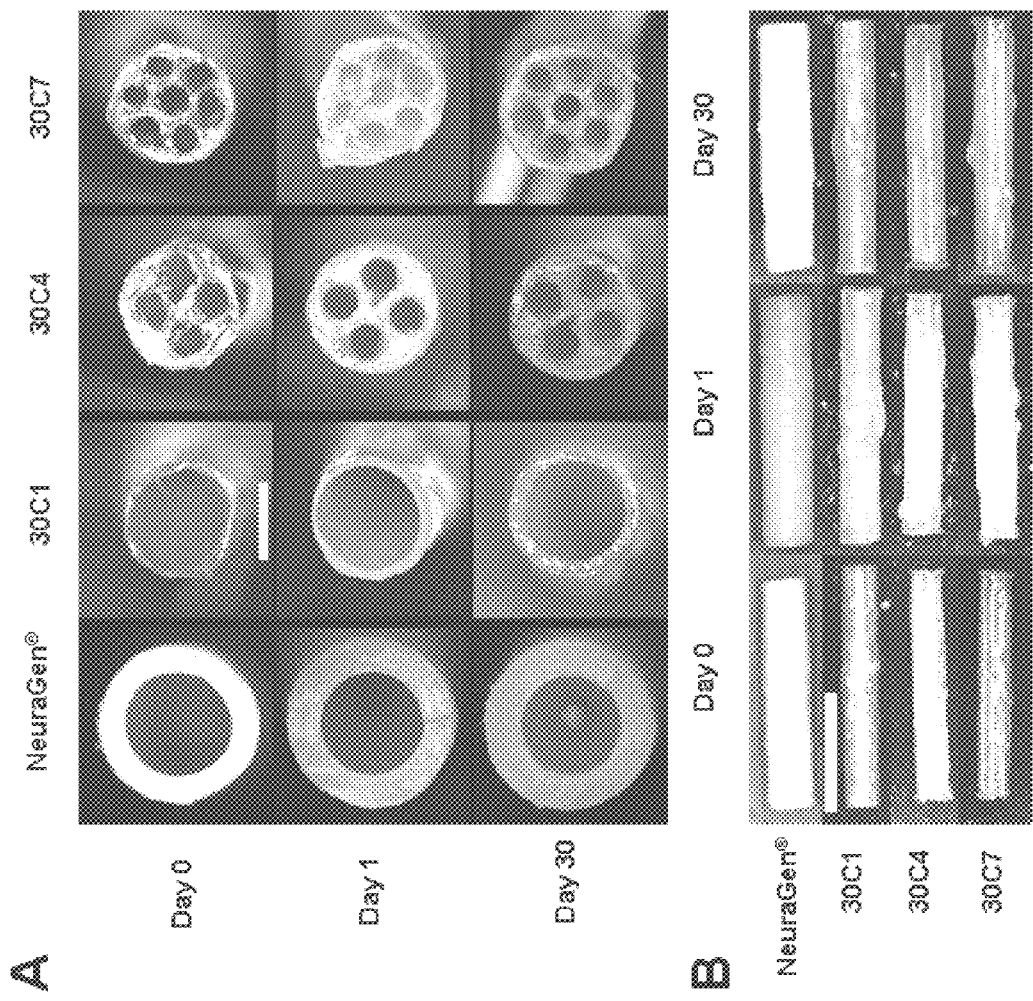
FIG. 6. The morphology of crosslinked 1-, 4-, 7-channel collagen conduits and Integra conduits after incubation in PBS at 37° C. (A) The transverse images of multichannel conduits. The multichannel collagen conduits maintained the channel morphology after 30 days incubation in PBS at 37° C. Scale bar, 1 mm. (B) The longitudinal images of multichannel conduits. Scale bar, 5 mm.
Figure 7:
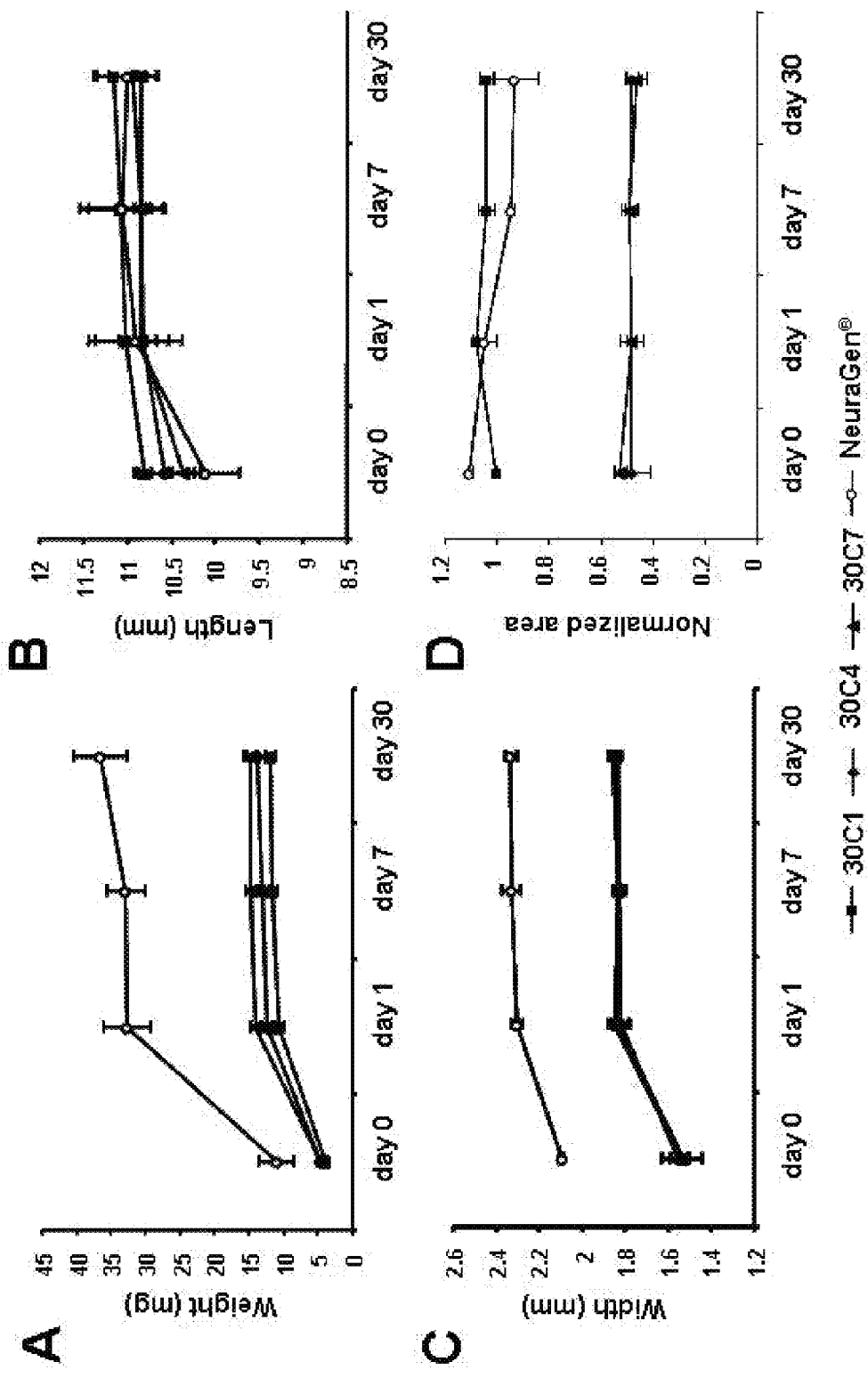
FIG. 7. Analysis of swelling study for crosslinked 1-, 4- and 7-channel collagen conduits and Integra collagen conduits. The morphology change of collagen conduits were measured in tube weight (A), length (B) width (C) and channel area (D) at the following time points: before incubation (day 0), 1 day, 7 days and 30 days incubation in PBS at 37° C.

After one day of incubation in PBS, the width and weight of all collagen conduits increased significantly (P<0.01); no significant changes were seen after day 1 (FIGS. 6 and 7). The length of 30C1, 30C4, and commercial conduits did not change significantly during the incubation period; however, the length of the 7-channel conduits increased significantly after 1 day incubation in PBS (P<0.05); no further significant changes were observed after 1 day. At day 30, the length of the conduits did not show significant variation between the types. The channel area of 4- and 7-channel conduits did not show significant change after incubation of 30 days. The channel area was normalized by calculating the ratio of the total open area in each conduit (in pixels) to the average area of the 1-channel conduits at day zero (prior to incubation). The channel area of the 1-channel conduits increased significantly (P<0.05) after 1 day incubation with no subsequent changes. The channel area of commercial conduits decreased significantly after 1 day incubation (P<0.05); no further significant changes were observed with incubation duration.

Figure 8:
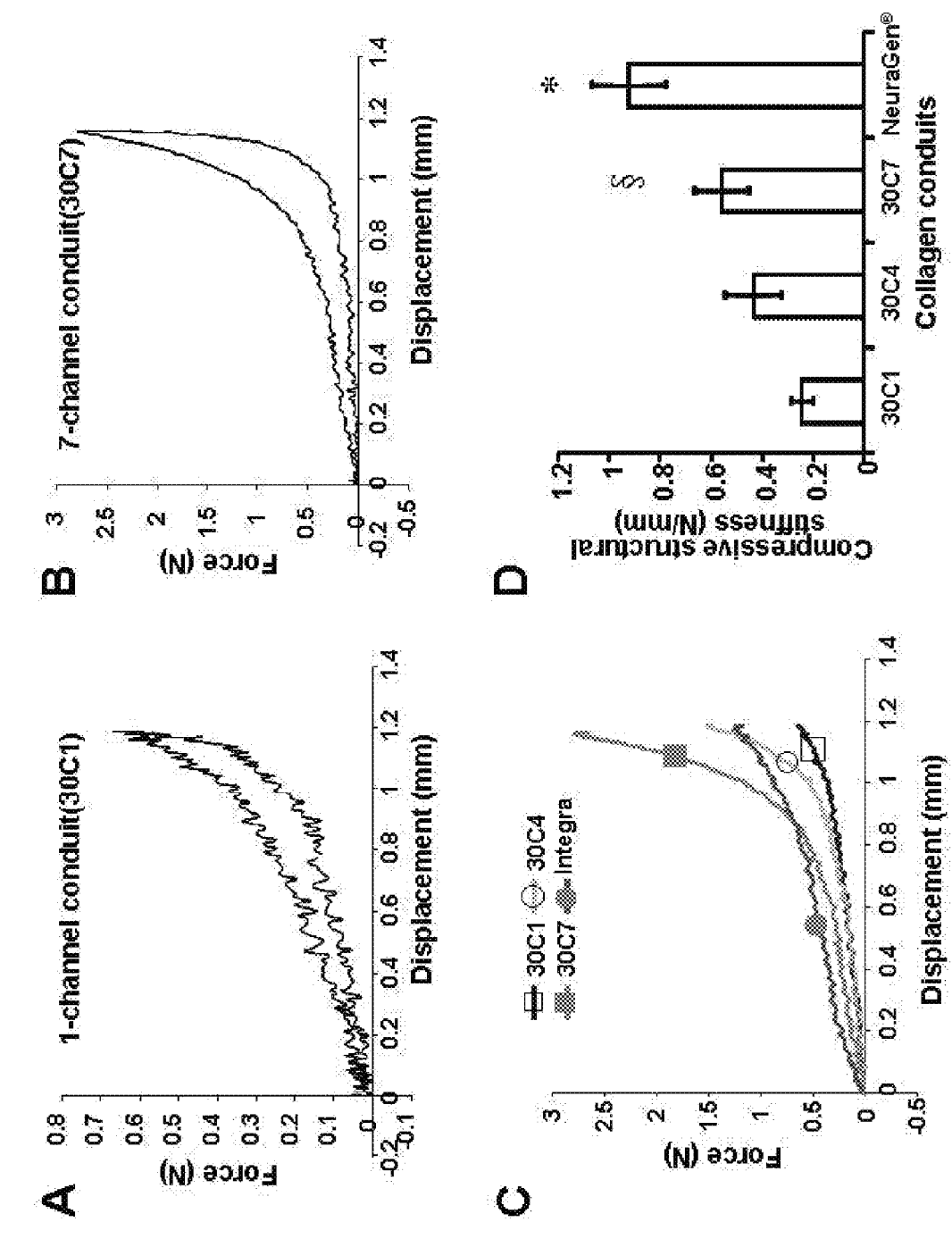
FIG. 8. Compressive study of collagen conduits. Representative loading and unloading compressive load-displacement curves for 30C1 (A) and 30C7 (B) conduits demonstrating nonlinear behavior with hysteresis but full elastic recoil. (C) Representative compressive load-displacement curve for each type of collagen conduit (loading only). (D) Transverse compressive structural stiffness of crosslinked collagen conduits. *, p<0.01, vs 30C1, 30C4 and 30C7 conduits. §, p<0.01, vs 30C1 conduits.

Multichannel Collagen Conduits Showed Greater Mechanical Stiffness and Strength than Single-Channel Collagen Conduits Results from the transverse compressive load-displacement analysis are shown in FIG. 8. The compressive load-displacement data for all types of conduits displayed the classic J-shaped curve characteristic of soft collagenous tissues with substantial hysteresis between the loading and unloading curves (FIGS. 8A and 8B). Full recovery of the initial dimensions was observed with no evidence of plastic deformation or crushing. Representative loading curves are shown in FIGS. 8C and 8D; note that the commercial conduit and 30C1 samples also increase in stiffness nonlinearly at displacements greater than 1.2 mm. For physiologic relevance, the initial linear portion of the curves prior to the toe-region was analyzed rather than the maximum slope. The transverse compressive structural stiffness of the commercial conduit was 0.92±0.15 N/mm (N=4), which was significantly higher than 30C1 (0.24±0.04 N/mm; N=4), 30C4 (0.43±0.11 N/mm; N=4) and 30C7 (0.56±0.11 N/mm; N=4) conduits (P<0.01). The compressive stiffness of the 30C7 conduit was significantly higher than that of the 30C1 conduits (P<0.01).

Figure 9:
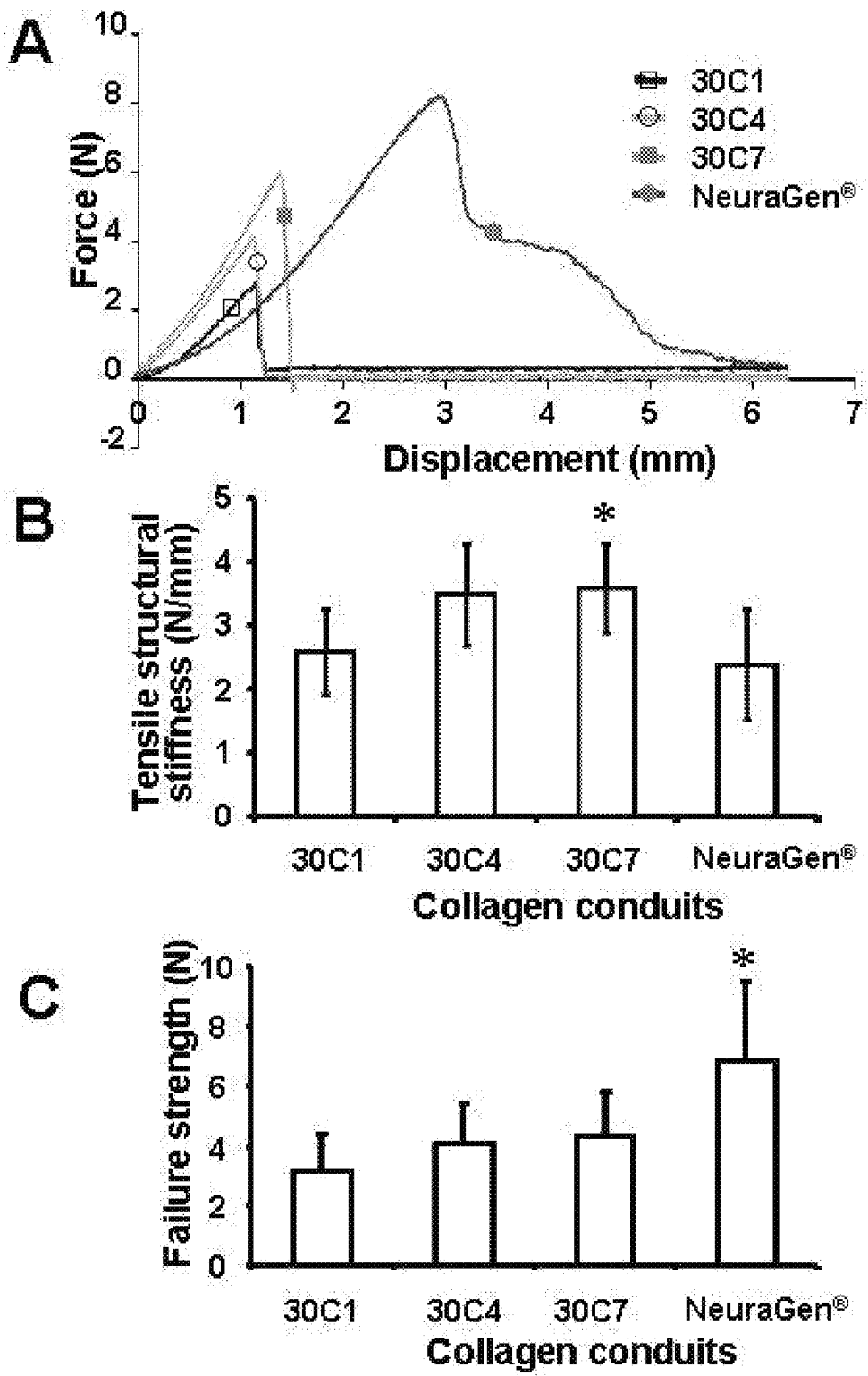
FIG. 9. Tensile study of collagen conduits. (A) Representative tensile load-displacement curves for each type of collagen conduit. (B) Tensile structural stiffness of crosslinked collagen conduits. *, p<0.05 vs 30C1 conduits. (C) The failure strength of the conduits (maximum force obtained). *, p<0.01 vs 30C1 conduits.

The tensile tests showed that the tensile structural stiffness of 30C7 conduits (3.59±0.70 N/mm; N=8) was significantly higher than the 30C1 conduits (2.57±0.66 N/mm; N=9; P<0.05). The tensile stiffness of 30C4 (3.48±0.80 N/mm; N=8) and commercial conduits (2.38±0.86 N/mm; N=3) were not significantly different from 30C1 and 30C7 conduits. The force applied to the commercial conduit at the failure point (6.89±2.6 N) was significantly higher than the 30C1 conduit (3.15±1.25 N; P<0.01) The forces at failure of the 30C4 and 30C7 conduits were not significantly different those of the 30C1 and commercial conduits (FIG. 9).

The data from the three-point bending study are shown in FIG. 10B. The bending stiffness of 30C1 conduits (0.77±0.28 Nmm$^2$; N=6) was significantly lower than 30C4 (1.88±0.35 Nmm$^2$; N=6; P<0.01) and 30C7 conduits (2.13±0.54 Nmm$^2$; N=6; P<0.01). The bending stiffness of 30C4 and 30C7 conduits was not significantly different. All of the samples returned to their original dimensions after the load was removed following maximal bending (>5 mm deflection)

Nerve Morphometry

Figure 11:
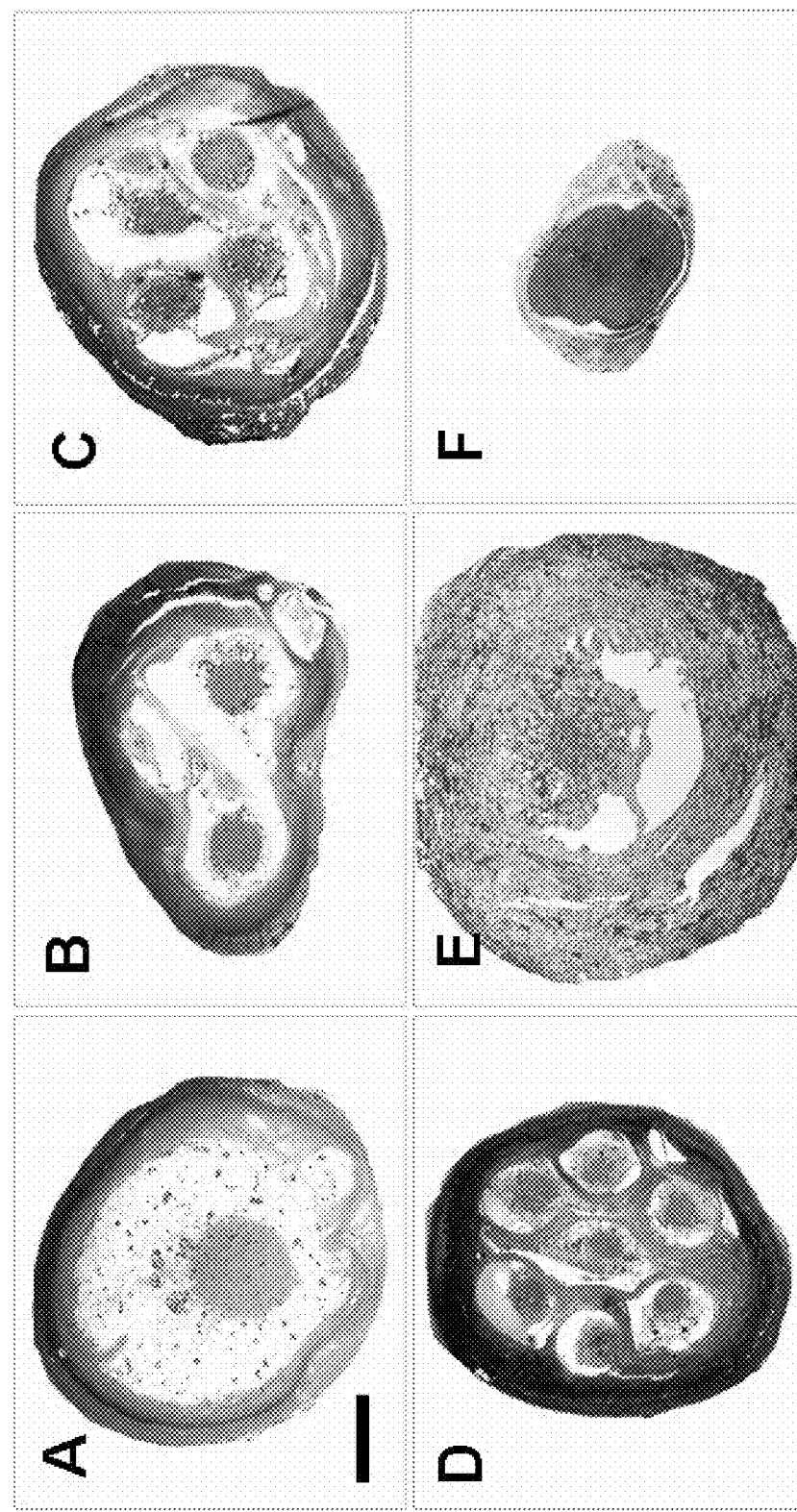
FIG. 11. Microscopic images (5× magnification) of sections stained with toluidine blue taken through the middle of an (A) 1-, (B) 2-, (C) 4-, and (D) 7-channel collagen conduit, (E) an NeuraGen® single channel conduit and (F) autograft. Scale bar, 500 µm.
Figure 12:
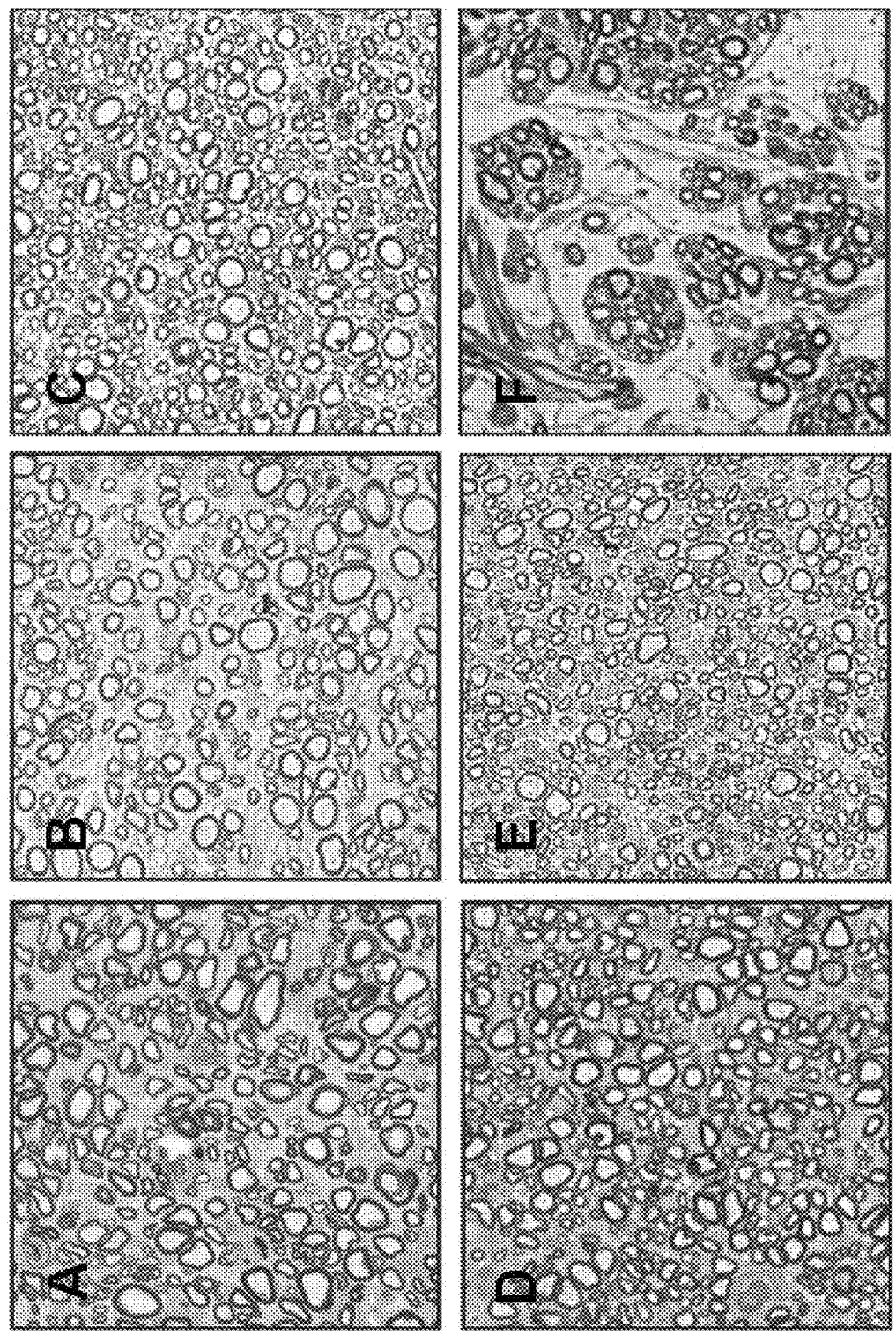
FIG. 12. Microscopic images (40× magnification) of sections stained with 1% phenylenediamine taken through the middle of an (A) autograft, (B) 1-, (C) 2-, (D) 4-, and (E) 7-channel collagen conduit and (F) an NeuraGen® single channel conduit. Scale bar, 30 µm.

Successful regeneration (defined for the presence of myelinated axons at the middle of the conduit) was observed in 39 out of 40 cases of conduit repair (in one 2-channel conduit graft only fibrous tissue was present). FIGS. 11 and 12 show microscopic images (taken at 5× magnification (FIG. 11) and 40× magnification (FIG. 12)) of sections taken through the middle of all 6 types of grafts.

Figure 13:
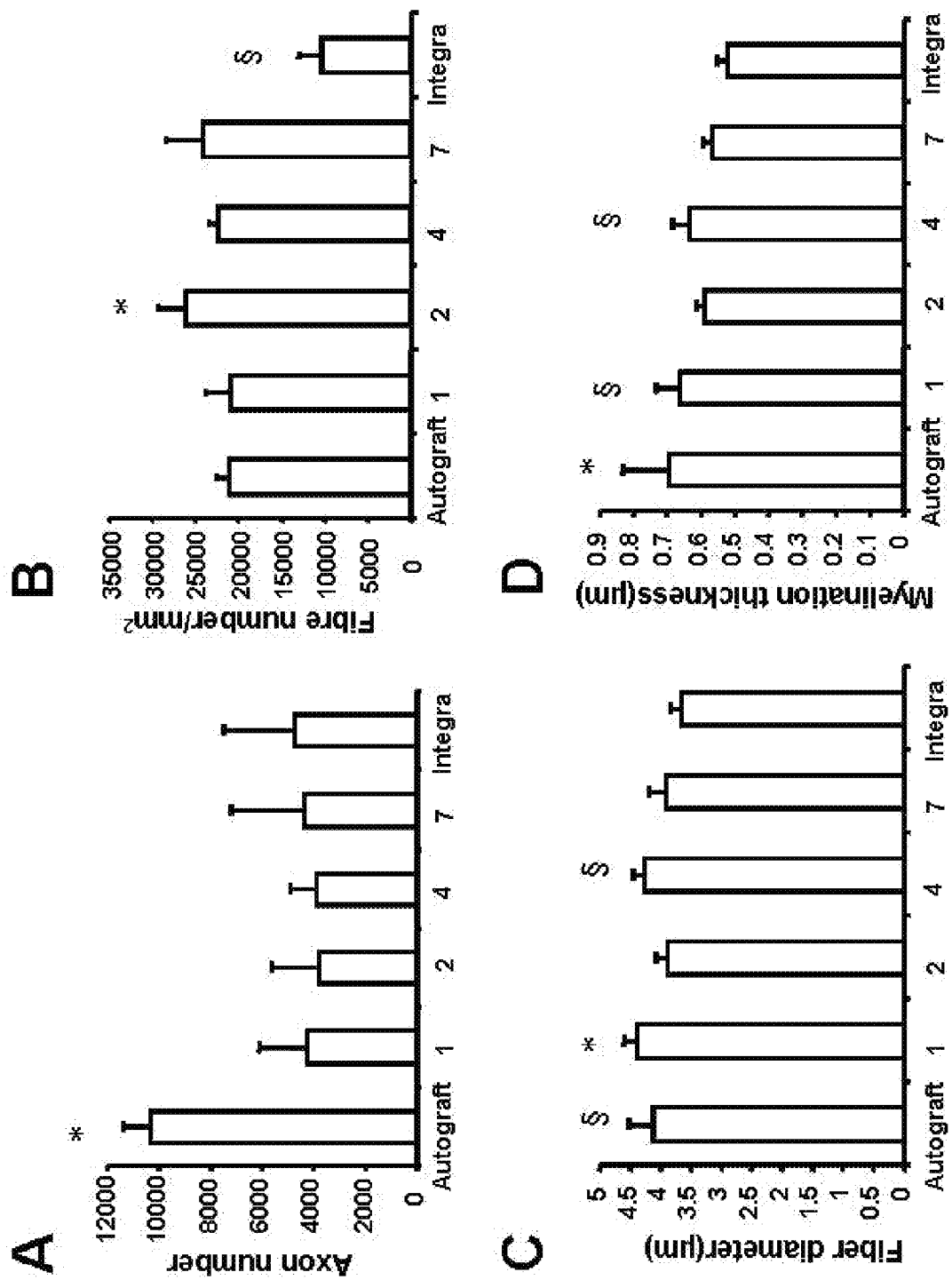
FIG. 13. Results of nerve morphometry after autograft, 1-, 2-, 4-, 7-channel collagen conduit and NeuraGen® conduit repair for (A) the mean number of myelinated fibers (*, P<0.01, vs all the conduit groups), (B) the mean myelinated fiber density (*, P<0.05, vs the autograft, single channel and 4-channel tube graft groups; §, P<0.01, vs all the other groups), (C) mean myelinated fiber size (*, P<0.01, vs 2-channel, 7-channel, NeuraGen® conduits; §, P<0.05, vs NeuraGen® conduit group), (D) mean myelin thickness (*, P<0.05, vs 7-channel and NeuraGen® conduit groups; §, P<0.05 vs NeuraGen® conduit group). Scale bar, 30 µm.

The mean number of fascicles (channels filled with myelinated axons) was one for the single channel conduits, 1.6±0.8 for the 2-channel conduits, 3.75±0.4 for the 4-channel conduits, and 6±1 for the 7-channel conduits. The mean number of myelinated fibers was not significantly different between conduit groups (FIG. 13A), but was significantly higher after autograft repair (10348±1038, vs all conduit groups, p<0.01). The mean density of myelinated fibers (FIG. 13B) was significantly higher for the 2-channel conduit group (vs autograft, 1-channel conduit, commercial conduit, p<0.05), and significantly lower for the commercial conduit group (vs all the other groups, P<0.01).

The myelinated fiber diameter (FIG. 13C) of the single-channel conduit group (4.37±0 µm) was significantly higher than the 2-, 7-channel and commercial conduit groups (p<0.01). The myelinated fiber diameter of the autograft and 4-channel conduit groups (4.08±0.37 µm and 4.27±0.19 µm respectively) were significantly higher than the commercial conduit graft group (3.64±0.20 μm; P<0.05). The myelination thickness (FIG. 13D) of the autograft group (0.67±0.13 μm) was significantly higher than those of the 7-channel conduit (0.57±0.03 μm; p<0.05) and commercial conduit groups (0.52±0.03 μm; p<0.01). The myelination thickness of the 1-channel and 4-channel conduit groups (0.66±0.07 μm and 0.64±0.0.05 μm respectively) was significantly higher than that of the commercial conduit group (p<0.05).

CMAPs

Figure 14:
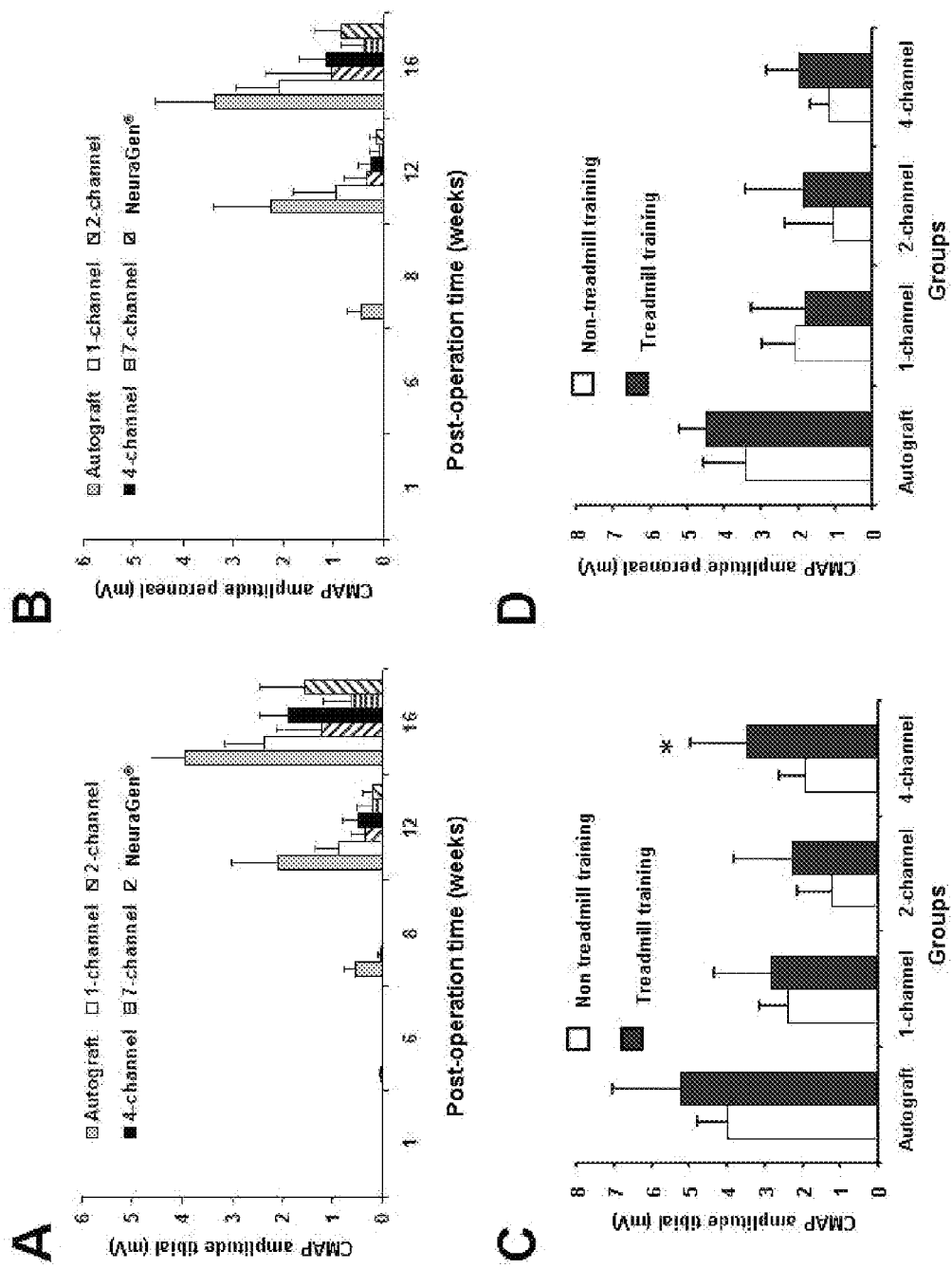
FIG. 14. Results of the mean amplitude for compound muscle action potentials recorded in plantar and dorsal foot muscle respectively in experimental group 1 (A and B). In panels C and D results are also presented for CMAP amplitudes in the animals in experimental group 2 that were trained with a treadmill (*, P<0.05).

In the first experimental group for the study of nerve morphometry and CMAP recording the first CMAPs were detected six weeks after autograft repair and eight weeks after single channel conduit repair (FIGS. 14A and B). The CMAP amplitude of all the experimental groups increased with time. At twelve weeks, the amplitude of the autograft group in the plantar muscles and dorsal foot muscles (2.08±0.94 mV and 2.25±1.16 mV respectively) was significantly higher than those of the other groups (p<0.01). At sixteen weeks, the CMAP amplitude of the autograft nerve in the plantar foot muscles and in the dorsal muscles (3.95±0.83 mV and 3.38±1.18 mV respectively) was significantly higher than those of the 2-, 4-, 7-channel and commercial conduit groups (p<0.01). The CMAP amplitude of the 1- and 4-channel conduit groups in the plantar foot muscles (2.35±0.80 mV and 1.90±0.70 mV respectively) was significantly higher than that of the 7-channel conduit group (0.63±0.56 mV, p<0.05). The CMAP amplitude of the 1-channel conduit group in the dorsal foot muscles (2.08±0.89 mV) was significantly higher than that of the 7-channel group (0.38±0.44 mV, p<0.01). The comparison of CMAPs at sixteen weeks was made between the first experimental group without treadmill training and the second experimental group with treadmill training in FIGS. 14C and D. The CMAP amplitude of the 4-channel group in the plantar foot muscles (3.43±0.70 mV) with treadmill training was significantly higher than that of the non-training group (p<0.05).

Simultaneous Retrograde Tracing

Figure 15:
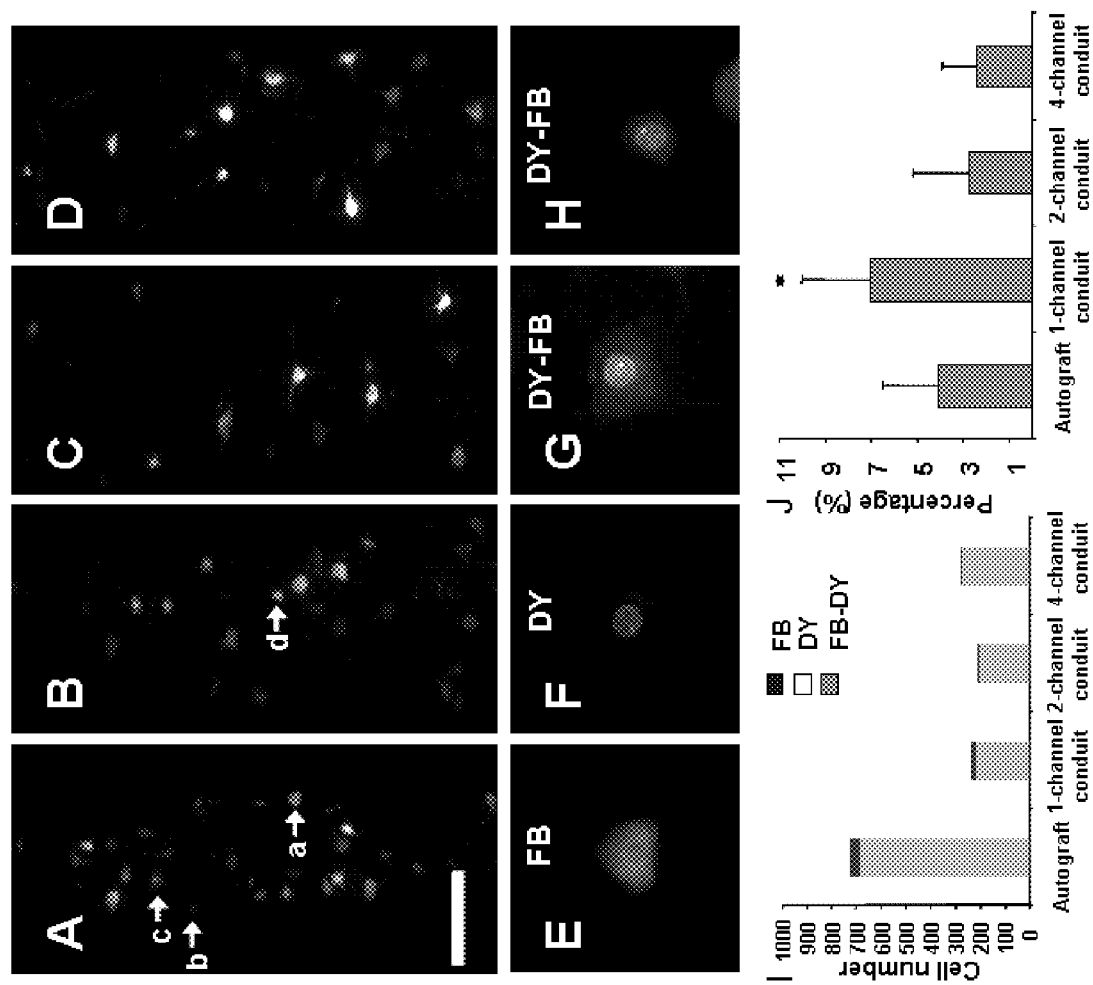
FIG. 15. A-D: Fluorescent microscopic images (10× magnification, DAPi filter) of longitudinal section taken through anterior horn after (A) autograft repair, (B) 1-channel, (C) 2-channel, and (D) 4-channel conduit repair. E-H: Fluorescent microscopic images (20× magnification, DAPi filter) of (E) a single FB-labeled profile (with blue cytoplasm and dark nucleus, arrow a), (F) single DY-labeled profile (with yellow nucleus and dark cytoplasm, arrow b), and (G and H) FB-DY double-labeled profiles (with yellow nucleus and blue cytoplasm. G, arrow c; H, arrow d). I: Results of simultaneous tracing for the mean number of FB-labeled, DY-labeled, and FB-DY double-labeled profiles after autograft, 1-, 2-, and 4-channel conduit repair. J: Results of simultaneous tracing for the percentages of double projections after autograft, 1-, 2-, and 4-channel conduit repair (*, P<0.05, vs 2-channel and 4-channel conduit groups). Scale bar, 200 µm.

After autograft, 1-, 2- and 4-channel conduit repair, FB-, DY-, and FB-DY-labeled profiles in the anterior horn in the spinal cord were found intermingled. Images of the differently labeled profiles are provided in FIG. 15. The total number of labeled profiles was not significantly different after 1-, 2- and 4-channel conduit repair, but was significantly higher after autograft repair (p<0.01). The percentage of double projections to both the tibial and peroneal nerve branch was calculated by dividing the total number of double labeled neurons by the total number of neurons (single-labeled (DY and FB) and double-labeled neurons). Interestingly, the percentage of double-labeled neurons was significantly smaller after 2-channel (2.7%±2.9%) and 4-channel conduit (2.4%±1.5%) repair, compared with single channel conduit repair (7.1%±2.7%) (both p<0.05), indicating less axonal dispersion after multichannel nerve tube repair.

Discussion

In designing the next generation of nerve conduits, the following characteristics of the conduits are desirable. The biomaterial should be biocompatible. The conduits ought to be flexible and possess sufficient mechanical strength to resist compression and collapse. The degradation of the conduits should be programmed to match the nerve regeneration rate. The manufacturing process of the biomaterial should be easy and reproducible.

In this study, by using a unique sequential moulding and air-dry technique in and/or with an optimized crosslinking method, we fabricated a series of multichannel collagen conduits with tailored biochemical and mechanical properties and demonstrated requisite cell compatibility. The dimensional stability, degradation rate, and mechanical properties of collagen can be regulated with a variety of crosslinking methods [Chau et al, 2005, Ben et al, 1988, Matsuda et al, 1999, Dunn et al, 1969]. However, cytotoxic effects of crosslinkers such as glutaraldehyde, hexamethylene diisocyanate, and acyl azidehas are well documented. EDC, a water-soluble zero-length crosslinker, can crosslink the molecules directly and, with repeated buffer and water washings, EDC has been shown to be less toxic than these "bridge-linking" crosslinkers.

To quantify the degree of crosslinking, the percentages of remaining free $—NH_2$ groups and shrink temperature of crosslinked collagen samples were studied. The mechanism of EDC crosslinking involves the activation of carboxylic groups (—COOH) of glutamic and aspartic acid residues and the formation of amide bonds (—CONH—) in the presence of free amine groups ($—NH_2$) of lysine or hydroxylysine residues. As EDC crosslinking involves the reaction between free —COOH groups and $—NH_2$ groups of collagen to form a —CONH-bond, crosslinking reduces the amount of free $—NH_2$ groups in collagen samples. The reduction of $—NH_2$ groups in collagen samples is consistent with the degree of collagen crosslinking DSC study showed that the shrink temperature of collagen samples increased when EDC concentration increased from 10 mM to 30 mM. This observation is consistent with the findings from ninhydrin studies and suggests that crosslinking with 30 mM EDC and 10 mM NHS creates the maximum number of crosslinking bridges. This result is supported by the maximal resistance to collagenase digestion of the conduits crosslinked with 30 mM EDC and 10 mM NHS. The swelling of collagen conduits is often observed in vivo and in vitro conditions. The initial swelling results from the uptake of water. Swelling may cause significant problems in in vivo application when it significantly deforms the conduits and decreases the conduits channel area. The deformation of nerve guides may impede the regenerating axonal outgrowth. The thickness and the swelling characteristics of collagen conduits may be controlled by crosslinking to make the tube stable. In this study we observed that the water uptake caused the channel area of Integra nerve conduits to decrease significantly after 1 day incubation in PBS at 37° C. In contrast, the channel area of fabricated 1-channel conduit did not show significant change. The control of swelling of the multichannel conduits is crucial, as the swelling of the interval between the channels may cause the significant reduction of the channel area. The swelling and deformation of Poly(lactide-co-glycolide) multichannel conduits have been shown in previous in vitro and in vivo studies [de Ruiter et al, 2008b] and the conduit cavities were consequently blocked. No nerve growth was seen in the blocked conduits. The multichannel collagen conduits fabricated in this study showed no channel area decrease in in vitro test and can also support the nerve growth in in vivo studies.

The mechanical properties of the nerve conduits are important for maintaining integrity and stability at the graft site. The nerve conduits must retain structural integrity when they are handled and implanted in the surgery. After surgery, the conduits need to provide sufficient biomechanical support during the process of nerve tissue regeneration. Specifically, the conduits must resist muscular contraction, stretching and distortion. In this study, collagen nerve conduits were designed with equal size of outer diameter and fabricated with a similar amount of collagen materials. Multichannel conduits showed greater structural stiffness than did our single-channel conduits in compressive, stretching and bending tests. Though NeuraGen® conduits showed higher compressive stiffness than multichannel collagen conduits, the amount of collagen required to create the NeuraGen® collagen conduits is three times that of the multichannel ones. These data, combined with the dimensional stability in the swelling tests and the resistance to enzymatic degradation in the collagenase assay, suggest that multichannel conduits crosslinked with 30 mM EDC will be mechanically superior to single-channel conduits in resisting deformation and maintaining channel geometry in vivo.

In addition to sufficient structural stiffness to resist external loading, we also observed that the conduits deform elastically under these substantial loads. Unlike the permanent deformation observed in three-point bending tests of multichannel PLGA conduits [de Ruiter, 2008a], we did not observe plastic deformation of the collagen-based multichannel conduits, even under large deformations. In addition, in all cases, no evidence of plastic deformation or crushing was observed in compressive tests to half of the diameter of the conduits. Combined, these results demonstrate elasticity of the conduits under substantial external loading and suggest that the conduits will remain pliable in the implantation environment. The flexibility and stiffness of multichannel conduits can be further adjusted by regulating wall thickness and number of channels The cytotoxic effect of the crosslinkers such as glutaraldehyde, hexamethylene diisocyanate, and acyl azidehas has been reported previously [Duan et al, 2005]. EDC is less toxic than these "bridge-linking" crosslinkers. Repeated buffer and water washing can remove the cytotoxic residues in the EDC and NHS crosslinked matrix [Pieper et al, 1999; Van wachem et al, 1994; Nieuwenhuis et al 1994a,b; Wissink et al, 2000]. However, the high concentration of EDC for crosslinking may result in cytotoxicity because of the limitation of —$NH_2$ groups in collagen for crosslinking reaction [Powell and Boyce, 2006]. In addition, cytotoxicity may result from the inadequate release of any unused EDC molecules or their reaction byproducts from the matrices through simple washing techniques. In this study, we showed there was no significant difference in the neurite outgrowth from DRGs growing on the natural collagen films, 10CF and 30CF films. However neurite growth is shorter from DRGs growing on collagen films crosslinked with 60 mM EDC.

In this study we showed that almost all channels contained fascicles with myelinated fibers. The amount of regeneration after repair with the different types of conduits was not significantly different despite the reduction in the total cross-sectional area for axons to grow into for multichannel nerve tubes. The ratios of total channel area for the 1-channel conduits versus 2-, 4- and 7-channel conduits are 4.1, 2.1 and 1.9, respectively. Similar findings were also observed in a previous study, though these results were limited by extensive swelling and collapse of the biomaterial poly(lactic co-glycolic acid) (PLGA) in the study [de Ruiter et al, 2008b]. CMAP examinations offer an important index for the conduction function of peripheral nerve. In this study, we observed the highest CMAP amplitude of autograft repair in both plantar foot muscles and dorsal muscles. This is consistent with its highest number of regenerated axons. One-channel and 4-channel conduit groups showed similar fiber diameter and myelination thickness to the autograft group. More immature fibers were seen in 2- and 7-channel and NeuraGen® conduit groups with smaller fiber diameter and myelination thickness which is related to the inferior amplitude values in the CMAP test. The quantitative results of regeneration in our study were still best for autograft repair. Autograft groups showed highest myelinated axon number, which is significantly higher than all the nerve conduit implanted groups. In this work, we used dual retrograde tracing to show the motor axon regeneration accuracy across single channel conduit and multichannel nerve conduits. The results of this study clearly demonstrate the potential influence that multichannel nerve tube structure have on limiting axonal dispersion across the conduit without decreasing the quantitative results of regeneration. After multichannel collagen conduit repair the percentage of motor neurons with double projections to both the tibial and peroneal nerve branch was three times smaller compared with single channel collagen conduit repair (2.4% vs 7.1%), while the total number of regenerated axons and motor neurons was equal. This suggested the nerve repair with multichannel conduits improved the accuracy of motor axon regeneration compared with that across single channel conduit without decreasing quantitative results of regeneration.

In this study, we show for the first time that nerve conduits with multiple sub-millimeter diameter channels can be reproducibly fabricated from purified collagen using a novel multi-step process. Optimized crosslinking conditions utilizing EDC yield high collagenase and thermal stability without influencing robust aonal growth from cultured DRGs. We demonstrate that multichannel conduits have mechanical properties superior to single-channel conduits created using similar processing techniques and properties comparable to NeuraGen®, a commercially available single-channel conduit containing three times more collagen per unit length. Compared to single channel tubes, multichannel conduits have the potential to provide superior target reinnervation by limiting the dispersion of regenerating axons and providing guidance for nerve growth. Taken together, the results suggest that 4- and 7-channel collagen conduits crosslinked with 30 mM EDC and 10 mM NHS possess favourable material and mechanical properties for nerve regeneration applications. The words "comprises/comprising" and "having/including" when used herein with reference to the present invention specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

REFERENCES

1. Archibald, S J., Krarup, C., Shefner, J. A Collagen-based Nerve Guide Conduit for Peripheral Nerve Repair An Electrophysiological Study of Nerve Regeneration in Rodents and non-human Primates. Journal of Comparative Neurology. 1991: 306: 685-696.
2. Bellamkonda R V. Peripheral nerve regeneration: an opinion on channels scaffolds and anisotropy. Biomaterials 2006; 27:3515-8.
3. Ben-Slimane, S., Guidoin, R., Marceau, D., Merhi, Y., King, M. W., Sigot-Luizard, M. F. Characteristics of polyester arterial grafts coated with albumin: The role and importance of the crosslinking chemicals. J Eur Surg Res 20, 18, 1988.
4. Bodine-Fowler S C, Meyer R S, Moskovitz A, Abrams R, Botte M J: Inaccurate projection of rat soleus motoneurons: A comparison of nerve repair techniques. Muscle Nerve 1997; 20:29-37.

5. Brushart T M, Mathur V, Sood R, Koschorke G M: Joseph H. Boyes Award: Dispersion of regenerating axons across enclosed neural gaps. J Hand Surg [Am] 1995; 20:557-564.
6. Cavalcanti R A, da Pureza D Y, de Melo M P, de Souza R R, Bergamaschi C T, do Amaral S L, Tang H, Loesch A, Ribeiro A A. Low-intensity treadmill exercise-related changes in the rat stellate ganglion neurons. J Neurosci Res. 2009 May 1; 87(6):1334.
7. Chau, D. Y., Collighan, R. J., Verderio, E. A., Addy, V. L., Grif• n, M. The cellular response to transglutaminase-cross-linked collagen. Biomaterials 26, 6518, 2005.
8. Chen C J, Ou Y C, Liao S L, Chen W Y, Chen S Y, Wu C W, Wang C C, Wang W Y, Huang Y S, Hsu S H. Transplantation of bone marrow stromal cells for peripheral nerve repair. Exp Neurol. 2007; 204:443-53.
9. Chen M H, Chen P R, Chen M H, Hsieh S T, Huang J S, Lin F H. An in vivo study of tricalcium phosphate and glutaraldehyde crosslinking gelatin conduits in peripheral nerve repair. J Biomed Mater Res B Appl Biomater. 2006; 77:89-97.
10. Chew, S. Y., Mi, R., Hoke, A., Leong, K. W. Aligned protein-polymer composite • bers enhance nerve regeneration: a potential tissue-engineering platform. Adv Funct Mater 17, 1288, 2007.
11. Collin, W., and Donoff, R B. Nerve Regeneration through Collagen Tubes. Journal of Dental Research. 1984: 63: 987-993.
12. de Ruiter G C, Spinner R J, Alaid A O, Koch A J, Wang H, Malessy M J, Currier B L, Yaszemski M J, Kaufman K R, Windebank A J. Two-dimensional digital video ankle motion analysis for assessment of function in the rat sciatic nerve model. J Peripher Nerv Syst. 2007; 12:216-22.
13. de Ruiter, G. C., Onyeneho, I. A., Liang, E. T., Moore, M. J., Knight, A. M., Malessy, M. J., Spinner, R. J., Lu, L., Currier, B. L., Yaszemski, M. J., Windebank, A. J. Methods for in vitro characterization of multichannel nerve tubes. J Biomed Mater Res A 84, 643, 2008b.
14. de Ruiter G C, Spinner R J, Malessy M J, Moore M J, Sorenson E J, Currier B L, Yaszemski M J, Windebank A J. Accuracy of motor axon regeneration across autograft, single-lumen, and multichannel poly(lactic-co-glycolic acid) nerve tubes. Neurosurgery. 2008a; 63:144-53; discussion 153-5.
15. Duan X, Sheardown H. Crosslinking of collagen with dendrimers. J Biomed Mater Res A 75, 510, 2005.
16. Dunn, M. W., Stenzel, K. H., Rubin, A. L., Miyata, T. Collagen implants in the vitreous. Arch Ophthalmol 82, 84, 1969.
17. English A W, Cucoranu D, Mulligan A, Sabatier M. Treadmill training enhances axon regeneration in injured mouse peripheral nerves without increased loss of topographic specificity. J Comp Neurol. 2009; 517:245-55.
18. Evans G R, Brandt K, Katz S. Bioactive poly (L-lactic acid) conduits seeded with Schwann cells for peripheral nerve regeneration. Biomaterials 2002; 23:841-8.
19. Evans P J, Bain J R, Mackinnon S E, Makino A P, Hunter D A: Selective reinnervation: A comparison of recovery following microsuture and conduit nerve repair. Brain Res 1991; 559:315-321.
20. Giannini, C., and Dyck, P J. The Fate of Schwann Cell Basement Membranes in Permanently Transected Nerves. Journal of Neuropathology and Experimental Neurology. 1990: 49: 550-563.
21. Iida H, Schmelzer J D, Schmeichel A M, Wang Y, Low P A. Peripheral nerve ischemia: reperfusion injury and fiber regeneration. Exp Neurol. 2003; 184:997-1002.
22. Jiang B G, Yin X F, Zhang D Y, Fu Z G, Zhang H B. Maximum number of collaterals developed by one axon during peripheral nerve regeneration and the in• uence of that number on reinnervation effects. Eur Neurol 2007; 58:12-20.
23. Jiao H, Yao J, Yang Y, Chen X, Lin W, Li Y, Gu X, Wang X. Chitosan/polyglycolic acid nerve grafts for axon regeneration from prolonged axotomized neurons to chronically denervated segments. Biomaterials. 2009; 30:5004-18.
24. Kim, Y. T., Haftel, K., Kumar, S., Bellamkonda, R. V. The role of aligned polymer • ber-based constructs in the bridging of long peripheral nerve gaps. Biomaterials 29, 3117, 2008.
25. Laquerriere, A., Jun, Y., Tiollier, J., Hemet, J., and Tadie, M. Experimental Evaluation of Bilayered Human Collagen as a Dural Substitute. Journal of Neurosurgery. 1993: 78: 487-491.
26. Matsuda, S., Iwata, H., Se, N., Ikada, Y. Bioadhesion of gelatin • lms cross-linked with glutaraldehyde. J Biomed Mater Res 45, 20, 1999.
27. Matsumoto K, Ohnishi K, Kiyotani T, Sekine T, Ueda H, Nakamura T, et al. Peripheral nerve regeneration across an 80-mm defect bridged by a polyglycolic acid (PGA)-collagen tube • lled with laminin-coated collagen • bers: a histological and electrophysiological evaluation of regenerated nerves. Brain Res 2000; 868:315-28.
28. O'Callaghan R M, Griffin E W, Kelly A M. Long-term treadmill exposure protects against age-related neurodegenerative change in the rat hippocampus. Hippocampus. 2009 Mar. 23. [Epub ahead of print]
29. Ozay R, Bekar A, Kocaeli H, Karli N, Filiz G, Ulus I H. Citicoline improves functional recovery, promotes nerve regeneration, and reduces postoperative scarring after peripheral nerve surgery in rats. Surg Neurol. 2007; 68:615-22.
30. Pieper, J. S., Oosterhof, A., Dijkstra, P. J., Veerkamp, J. H., van Kuppevelt, T. H. Preparation and characterization of porous crosslinked collagenous matrices containing bio-available chondroitin sulphate. Biomaterials 20, 847, 1999.
31. Powell, H. M., Boyce, S. T. EDC cross-linking improves skin substitute strength and stability. Biomaterials 27, 5821, 2006.
32. Rodriguez, F J, et al; (1999) Highly permeable polyactide-caprolactone nerve guides enhance peripheral nerve regeneration through long gaps. Biomaterials 20(16); 489-500.
33. Sakakima H, Yoshida Y, Sakae K, Morimoto N. Different frequency treadmill running in immobilization-induced muscle atrophy and ankle joint contracture of rats. Scand J Med Sci Sports. 2004; 14:186-92.
34. Sabatier M J, Redmon N, Schwartz G, English A W. Treadmill training promotes axon regeneration in injured peripheral nerves. Exp Neurol. 2008; 211:489-93.
35. Sorenson, E J., and Windebank, A J. Relative Importance of Basement Membrane and Soluble Growth Factors in Delayed and Immediate Regeneration of Rat Sciatic Nerve. Journal of Neuropathology and Experimental Neurology. 1993: 52: 216-222.
36. Thomas F, Rivelino M, Hui S K, Molly S S. Chitin-based tubes for tissue engineering in the nervous system. Biomaterials 2005; 26: 4624-32.
37. Ta, L. E., Espeset, L., Podratz, J., Windebank, A. J. Neurotoxicity of oxaliplatin and cisplatin for dorsal root ganglion neurons correlates with platinum-DNA binding. Neurotoxicol. 27, 992, 2006.

38. Toba T, Nakamura T, Lynn A K, Matsumoto K, Fukuda S, Yoshitani M, et al. Evaluation of peripheral nerve regeneration across an 80-mm gap using a polyglycolic acid (PGA)-collagen nerve conduit • lled with laminin-soaked collagen sponge in dogs. Int J Artif Organs 2002; 25:230-7.
39. van Wachem, P. B., van Luyn, M. J., Olde Damink, L. H., Dijkstra, P. J., Feijen, J., Nieuwenhuis, P. Biocompatibility and tissue regenerating capacity of crosslinked dermal sheep collagen. J Biomed Mater Res 28, 353, 1994a.
40. van Wachem, P. B., van Luyn, M. J., Olde Damink, L. H., Dijkstra, P. J., Feijen, J., Nieuwenhuis, P. Tissue regenerating capacity of carbodiimide-crosslinked dermal sheep collagen during repair of the abdominal wall. Int J Artif. Organs 17, 230, 1994b.
41. Vleggeert-Lankamp C L, de Ruiter G C, Wolfs J F, Pègo A P, Feirabend H K, Lakke E A, Malessy M J: Type grouping in skeletal muscles after experimental reinnervation: Another explanation. Eur J Neurosci 2005; 21:1249-1256.
42. Wang X, Hu W, Cao Y, Yao J, Wu J, Gu X. Dog sciatic nerve regeneration across a 30-mm defect bridged by a chitosan/PGA artificial nerve graft. Brain. 2005; 128:1897-910.
43. Wang W, Itoh S, Matsuda A, Aizawa T, Demura M, Ichinose S, Shinomiya K, Tanaka J Enhanced nerve regeneration through a bilayered chitosan tube: the effect of introduction of glycine spacer into the CYIGSR sequence. J Biomed Mater Res A. 2008 Jun. 15; 85:919.
44. Wissink, M. J., van Luyn, M. J., Beernink, R., Dijk, F., Poot, A. A., Engbers, G. H., Beugeling, T., van Aken, W. G, Feijen, J. Endothelial cell seeding on crosslinked collagen: effects of crosslinking on endothelial cell proliferation and functional parameters. Thromb Haemostasis 84, 325, 2000.
45. Yang Y, Ding F, Wu J, Hu W, Liu W, Liu J, Gu X. Biomaterials. 2007; 28:5526-35. Development and evaluation of silk fibroin-based nerve grafts used for peripheral nerve regeneration.
46. Yao, L., O'Brien, N., Windebank, A., Pandit, A. Orienting neurite growth in electrospun fibrous neural conduits. J Biomed Mater Res B Appl Biomater 90, 483, 2009 (1).
47. Yao, L., Wang, S., Cui, W., Sherlock, R., O'Connell, C., Damodaran, G., Gorman, A., Windebank, A., Pandit, A. Effect of functionalized micropatterned PLGA on guided neurite growth. Acta Biomater 5, 580, 2009 (2).

The invention claimed is:

1. A method of manufacturing a collagen multichannel nerve conduit comprising:
  (a) placing at least one elongate former between two retainers of a multichannel nerve conduit mould such that, when there are two or more formers, the formers are held in a spaced-apart relationship to each other,
  (b) pouring a collagen solution over each former to coat substantially the at least one former,
  (c) drying the collagen solution on the at least one former,
  (d) repeating steps (a) to (c) with additional former(s) wherein the total number of formers are the same as the number of channels desired in the conduit,
  (e) cross-linking the dried collagen using a cross-linker, and
  (f) washing the cross-linked collagen to remove the cross-linker.

2. A method of manufacturing a collagen multichannel nerve conduit comprising:
  (a) placing at least one elongate former between two retainers,
  (b) pouring a collagen solution over the at least one former to coat substantially the at least one former,
  (c) air-drying the collagen solution on the at least one former,
  (d) cross-linking the dried collagen using a cross-linker, and
  (e) washing the cross-linked collagen to remove the cross-linker.

3. The method as claimed in claim 1 or 2 wherein additional collagen solution is poured around the dried collagen and/or poured around the retainer.

4. The method as claimed in claim 1 or 2 wherein the collagen concentration in the collagen solution is between 3 and 15 mg/ml.

5. The method as claimed in claim 1 or 2 wherein the cross-linker is selected from the group consisting of (1-ethyl-3-(3-dimethylaminopropyl) carbodiimide (EDC), transglutaminase, glutaraldehyde, genepin, sulfonates, malemide, polyethylene glycol dendrimeric systems, dendritic polymers, hyper-branced dendritic polymers, formaldehyde, enzymatic cross-linker, glycation, glyceraldehydes, cyanamide, diimide, diisocyante, dimethyl adipimidate, carbodiimide and epoxy.

6. The method as claimed in claim 5 wherein the dried collagen is cross-linked with 1-60 mM EDC and 1-30 mM N-hydroxysuccinimide (NHS) in 1-100 mM 2-(N-morpholino)ethanesulfonic acid (MES) solution.

7. The method as claimed in claim 1 or 2 wherein the washing step is carried out with 0.1-0.2 M $NaH_2PO_4$ and distilled water.

8. The method as claimed in claim 1 or 2 further comprising the step of freeze-drying the collagen after the washing step.

9. The method as claimed in claim 1 or 2 further comprising the step of removing the collagen nerve conduit from the former.

10. The method as claimed in claim 1 or 2 wherein the former is a metal wire.

11. The method as claimed in claim 1 or 2 wherein two to two hundred formers are used between the retainers.

12. The method as claimed in claim 1 or 2 wherein the formers are evenly sized and evenly spaced apart.

13. The method as claimed in claim 1 or 2 wherein the collagen is type I collagen.

14. The method as claimed in claim 1 or 2 further comprising the step of tethering biomolecules to the collagen.

15. The method of claim 4, wherein the collagen concentration in the collagen solution is 12 mg/ml.

16. The method of claim 5, wherein the sulfonate is methyl sulfonate or trifluoromethyl sulfonate.

17. The method of claim 5, wherein the polyethylene glycol dendrimeric system is poly(ethylene glycol) ether tetrasuccinimidyl glutarate (4S-StarPEG).

18. The method of claim 5, wherein the dried collagen is cross-linked with 30 mM EDC and 10 mM NHS in 50 mM MES solution.

19. The method of claim 11, wherein 2, 4 or 7 formers are used.

20. The method of claim 13, wherein the collagen is bovine tendon collagen.

21. The method of claim 14, wherein the biomolecule is selected from the group consisting of nucleic acids, peptides, laminin, and nerve growth factors.

22. The method of claim 21, wherein the nucleic acid is plasmid DNA or siRNA.

23. The method of claim 21, wherein the nerve growth factor is NGF or NT3.

* * * * *